United States Patent
Ostergard

(10) Patent No.: US 11,992,428 B1
(45) Date of Patent: *May 28, 2024

(54) HINGED ANKLE BRACE

(71) Applicant: Doak Ostergard, Lincoln, NE (US)

(72) Inventor: Doak Ostergard, Lincoln, NE (US)

( * ) Notice: Subject to any disclaimer, the term of this patent is extended or adjusted under 35 U.S.C. 154(b) by 527 days.

This patent is subject to a terminal disclaimer.

(21) Appl. No.: 17/350,154

(22) Filed: Jun. 17, 2021

Related U.S. Application Data

(63) Continuation-in-part of application No. 17/323,318, filed on May 18, 2021, now Pat. No. 11,737,902.

(51) Int. Cl.
   A61F 5/01 (2006.01)
   A61F 5/37 (2006.01)

(52) U.S. Cl.
   CPC .......... *A61F 5/0127* (2013.01); *A61F 5/3761* (2013.01); *A61F 2005/0137* (2013.01); *A61F 2005/0165* (2013.01)

(58) Field of Classification Search
   CPC .... A61F 5/0111; A61F 5/0113; A61F 5/0106; A61F 5/0127; A61F 5/3761; A61F 5/37; A61F 2005/0148; A61F 2005/0179; A61F 2005/0165; A61F 2005/0169; A61F 2005/0197; A61F 2005/0137; Y10T 403/455; Y10T 403/454; Y10T 403/32541; Y10T 403/32549; Y10T 403/32557; Y10T 403/45; Y10T 403/458; A63B 21/4025; A63B 21/4013; A63B 21/04–0407; A63B 21/0421; A63B 21/045
   USPC .............................................. 403/22; 602/16
   See application file for complete search history.

(56) References Cited

U.S. PATENT DOCUMENTS

| | | | |
|---|---|---|---|
| 4,934,355 A | 6/1990 | Porcelli | |
| 5,069,202 A | 12/1991 | Prock | |
| 5,209,716 A | 5/1993 | Frydman et al. | |
| 5,263,911 A * | 11/1993 | Frydman ................ | A63B 23/08 482/79 |
| 7,753,866 B2 | 7/2010 | Jackovitch | |
| 8,641,654 B2 | 2/2014 | Verkade et al. | |
| 9,364,366 B2 | 6/2016 | Verkade et al. | |
| 10,226,373 B1 | 3/2019 | McCoy | |
| 11,045,343 B2 | 6/2021 | Ostergard | |
| 2006/0084899 A1 | 4/2006 | Verkade et al. | |
| 2011/0226385 A1 | 9/2011 | Mitchell et al. | |

(Continued)

FOREIGN PATENT DOCUMENTS

| | | |
|---|---|---|
| WO | 2010070364 A1 | 6/2010 |
| WO | WO2010070364 A1 | 6/2010 |

*Primary Examiner* — Alireza Nia
*Assistant Examiner* — Daniel A Miller
(74) *Attorney, Agent, or Firm* — Suiter Swantz PC LLO

(57) ABSTRACT

A hinged ankle brace including a foot bed member and an ankle cuff which are hinged together by flexible joint members. The flexible joint members yieldably resist hinged movement between the foot bed member and the ankle cuff in a plantarflexion and dorsiflexion direction. Disc-shaped spacer-washers are positioned at the outer sides of the flexible joint members. The design of the upper ends of the medial and lateral wings of the foot bed member and the ankle cuff permits a limited amount of inversion and eversion movement between the foot bed member and the ankle cuff. The flexible joint members and the spacer-washers also permit a limited amount of inversion and eversion between the foot bed member and the ankle cuff.

6 Claims, 19 Drawing Sheets

(56) References Cited

U.S. PATENT DOCUMENTS

| | | |
|---|---|---|
| 2013/0075966 A1 | 3/2013 | Carvey et al. |
| 2014/0066829 A1 | 3/2014 | Drillio |
| 2015/0216703 A1 | 8/2015 | Madden et al. |
| 2018/0153724 A1* | 6/2018 | Ostergard ............ A61F 5/0127 |

* cited by examiner

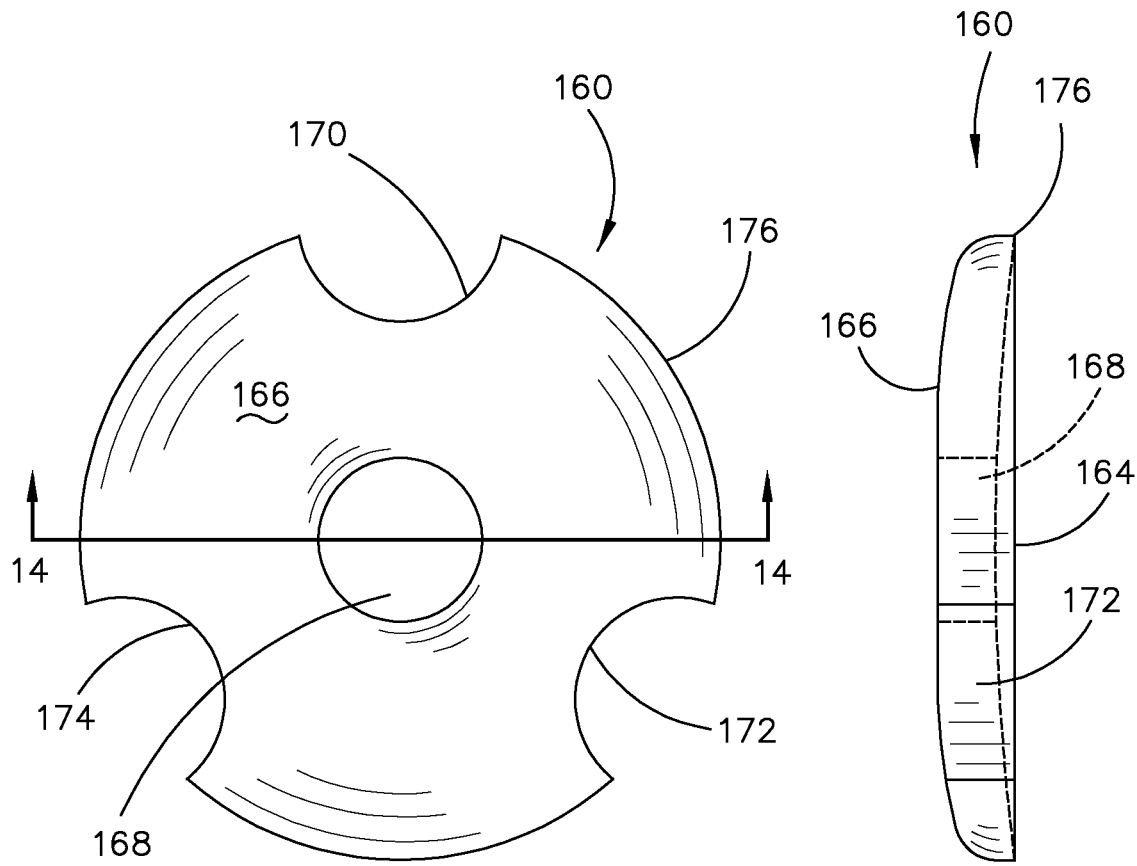
FIG. 12
FIG. 13
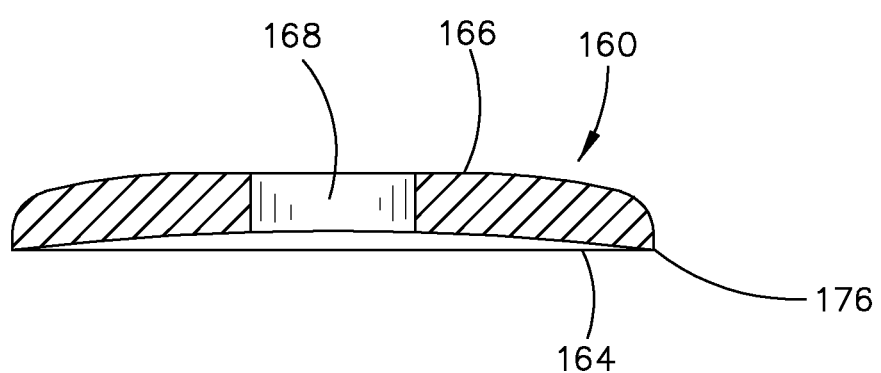
FIG. 14

HINGED ANKLE BRACE

CROSS REFERENCE TO RELATED APPLICATION

This is a Continuation-In-Part Application of application Ser. No. 17/323,318, now U.S. Pat. No. 11,737,902, filed May 18, 2021, entitled A HINGED ANKLE BRACE.

BACKGROUND OF THE INVENTION

Field of the Invention

This invention relates to a hinged ankle brace and more particularly relates to a hinged ankle brace wherein the medial and lateral joints between the foot bed member and the ankle cuff are flexible joint members comprised of polyurethane or like materials. Even more particularly, a disc-shaped spacer-washer is associated with each of the flexible joint members. Even more particularly, the flexible joint members create greater resistance to hinged movement of the foot bed member and the ankle cuff thereof as the two members hingedly move to a greater degree with respect to one another. Even more particularly, the flexible joint members and the spacer-washers and related structure not only permit plantarflexion and dorsiflexion hinged movement between the foot bed member and the ankle cuff but also permit inversion and eversion movement therebetween.

Description of the Related Art

Conventional semi-rigid ankle braces have been previously provided wherein the foot bed member of the ankle brace is pivotally or hingedly movable, about a pair of joints, with respect to the ankle cuff of the brace or vice versa. Normally, each of the prior art joints between the foot bed member and the ankle cuff are simply a pivot pin or bolt. In such braces, the pivotal movement between the foot bed member and the ankle cuff is not a floating movement but is a pivotal movement about a central axis. Further, to the best of Applicant's knowledge, no one other than Applicant has provided a joint for hinged ankle braces which increases the resistance to pivotal movement as the pivotal movement between the foot bed member and the ankle cuff increases. In other words, in the prior art, any resistance to the pivotal movement between the foot bed member and the ankle cuff, if any, remains the same during the entire pivotal movement therebetween.

Applicant's hinged ankle brace of Published Application U.S. 2018/0153724 A1 represents a significant advance in the ankle brace art in that the flexible joint members thereof create greater resistance to hinged movement of the foot bed member and the ankle cuff thereof as the two members hingedly move to a greater degree with respect to one another. However, the flexible joint members of the co-pending published application only permit plantarflexion and dorsiflexion movement of the foot bed member and the ankle cuff thereof. Applicant has determined that it is advantageous to also permit some inversion and eversion movement between the foot bed member and the ankle cuff thereof. The invention of patent application Ser. No. 17/323,318 permits additional inversion and eversion movement between the foot bed member and the ankle cuff thereof. The hinged ankle brace of the invention as shown and described in patent application Ser. No. 17/323,318 represents an advance in the art. The instant invention represents a further advance in the art.

SUMMARY OF THE INVENTION

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

With respect to the hinged ankle brace of FIGS. 1-17, the hinged ankle brace includes a foot bed member having a foot plate configured to underlie at least a portion of the foot of the wearer and a portion configured to receive a heel of the wearer. For purposes of description, the foot bed member is described as having a medial side and a lateral side. The hinged ankle brace of FIGS. 1-17 is described as being attached to the left ankle and foot of the wearer. If the hinged ankle brace of FIGS. 1-17 is attached to the right ankle and foot of the wearer, the medial side of the foot bed member will become the lateral side of the foot bed member and the lateral side of the foot bed member will become the medial side of the foot bed member.

With respect to the hinged ankle brace of FIGS. 1-17, a medial wing extends upwardly from the medial side of the foot bed member with the medial wing having a semi-circular upper end with inner and outer sides. The inner side of the upper end of the medial wing of the foot bed member may be outwardly curved. The outer side of the upper end of the medial wing of the foot bed member may be outwardly curved or domed. The upper end of the medial wing of the foot bed member has radially spaced-apart first, second and third curved slots formed therein. The upper end of the medial wing of the foot bed member has a central section with a central opening formed therein. Radially spaced-apart first, second and third pin members extend outwardly from the outer side of the central section thereof.

With respect to the hinged ankle brace of FIGS. 1-17, the hinged ankle brace includes a disc-shaped medial spacer-washer positioned at the outer side of the central section of the medial wing of the foot bed member. The medial spacer-washer has an inner side and an outer side and has a central opening formed therein. The periphery of the medial spacer-washer has first, second and third radially spaced-apart semi-circular openings formed therein. The central opening of the medial spacer-washer registers with the central opening in the central section of the upper end of the medial wing of the foot bed member. The first, second and third semi-circular openings at the periphery of the medial spacer-washer receive the first, second and third pin members which extend outwardly from the outer side of the central section thereof.

With respect to the hinged ankle brace of FIGS. 1-17, the hinged ankle brace includes a lateral wing which extends upwardly from the lateral side of the foot bed member and has a generally semi-circular upper end with inner and outer sides. The inner side of the upper end of the lateral wing of the foot bed member may be outwardly curved. The outer side of the lateral wing may be outwardly curved or domed. The upper end of the lateral wing of the foot bed member has radially spaced-apart first, second and third curved slots formed therein. The lateral wing of the foot bed member has a central section with a central opening formed therein. Radially spaced-apart first, second and third pin members extend outwardly from the outer side of the central section thereof.

With respect to the hinged ankle brace of FIGS. 1-17, the hinged ankle brace includes a disc-shaped lateral spacer-washer positioned at the outer side of the central section of the lateral wing of the foot bed member. The lateral spacer-washer has an inner side and an outer side and has a central opening formed therein. The periphery of the lateral spacer-washer has first, second and third radially spaced-apart semi-circular openings formed therein. The central opening in the lateral spacer-washer of the upper lateral wing member registers with the central opening in the central section of the upper end of the lateral wing of the foot bed member. The first, second and third semi-circular openings in the periphery of the lateral spacer-washer receive the first, second and third pin members which extend outwardly from the outer side of the central section thereof.

With respect to the hinged ankle brace of FIGS. 1-17, the ankle brace also includes an ankle cuff, having upper and lower ends and also includes a leg-supported portion configured to extend at least partially around the posterior side of the lower leg of a wearer. The ankle cuff has a medial side and a lateral side. The ankle cuff has a medial wing which extends downwardly from the medial side thereof. The medial wing of the ankle cuff has a generally semi-circular lower end with inner and outer sides. The inner side of the medial wing of the ankle cuff may be outwardly curved. The outer side of the medial wing of the ankle cuff may be outwardly curved or domed. The lower end of the medial wing of the ankle cuff has radially spaced-apart first, second and third curved slots formed therein. The lower end of the medial wing of the ankle cuff has a central section with a central opening formed therein. Radially spaced-apart first, second and third pin members extend inwardly from the inner side of the lower end of the medial wing of the ankle cuff.

With respect to the hinged ankle brace of FIGS. 1-17, the ankle cuff also has a lateral wing extending downwardly from the lateral side thereof. The lateral wing of the ankle cuff has a generally semi-circular lower end with inner and outer sides. The inner side of the lateral wing of the ankle cuff may be outwardly curved. The outer side of the lateral wing of the ankle cuff may be outwardly curved or domed. The lower end of the lateral wing of the ankle cuff has radially spaced-apart first, second and third curved slots formed therein. The lower end of the lateral wing of the ankle cuff has a central section with a central opening formed therein. Radially spaced-apart first, second and third pin members extend inwardly from the inner side of the lower end of the lateral wing of the ankle cuff.

With respect to the hinged ankle brace of FIGS. 1-17, the inner side of the lower end of the medial wing of the ankle cuff is positioned outwardly of the outer side of the upper end of the medial wing of the foot bed member. The inner side of the lower end of the lateral wing of the ankle cuff is positioned outwardly of the outer side of the upper end of the lateral wing of the foot bed member.

With respect to the hinged ankle brace of FIGS. 1-17, a flat flexible medial joint member is positioned between the lower end of the medial wing of the ankle cuff and the upper end of the medial wing of the foot bed member. The flexible medial joint member includes a central base portion having radially spaced-apart first, second and third pin openings formed therein. The base portion of the flexible medial joint member has a central opening formed therein. The flexible medial joint member has radially spaced-apart first, second and third arms with inner and outer ends, extending outwardly from the base portion thereof. Fourth, fifth and sixth pin openings are formed in the outer ends of the first, second and third arms respectively.

As stated, the flexible medial joint member of FIGS. 1-17 is positioned at the inner side of the lower end of the medial wing of the ankle cuff. When so positioned, the first, second and third pin members, which extend inwardly from the inner side of the lower end of the medial wing of the ankle cuff, are received in the fourth, fifth and sixth pin openings in the flexible medial joint member respectively. The disc-shaped medial spacer-washer is positioned at the inner side of the flexible medial joint member. In that position, the first, second and third pin openings in the flexible medial joint member register with the first, second and third slots formed in the lower end of the medial wing of the ankle cuff and the central opening in the base portion of the flexible medial joint member registers with the central opening formed in the central section of the lower end of the medial wing of the ankle cuff. A connector element, such as a rivet or the like, extends through the central opening in the lower end of the medial wing of the ankle cuff, through the central opening in the base portion of the flexible medial joint member, through the central opening in the medial spacer-washer, and through the central opening in the central section of the upper end of the medial wing of the foot bed member to hingedly connect the medial wing of the foot bed member to the medial wing of the ankle cuff.

With respect to the hinged ankle brace of FIGS. 1-17, a flat flexible lateral joint member is positioned between the lower end of the lateral wing of the ankle cuff and the upper end of the lateral wing of the foot bed member. The flexible lateral joint member includes a central base portion having radially spaced-apart first, second and third pin openings formed therein. The base portion of the flexible lateral joint member has a central opening formed therein. The flexible lateral joint member has first, second and third arms with inner and outer ends, extending outwardly from the base portion thereof. Fourth, fifth and sixth pin openings are formed in the outer ends of the first, second and third arms respectively.

As stated, the flexible lateral joint member of FIGS. 1-17 is positioned at the inner side of the lower end of the lateral wing of the ankle cuff. When so positioned, the first, second and third pin members, which extend inwardly from the inner side of the lower end of the lateral wing of the ankle cuff, are received in the fourth, fifth and sixth pin openings in the flexible lateral joint member respectively. The disc-shaped lateral spacer-washer is positioned at the inner side of the flexible lateral member. In that position, the first, second and third pin openings in the flexible lateral joint member register with the first, second and third slots formed in the lower end of the lateral wing of the ankle cuff and the central opening in the base portion of the flexible lateral joint member registers with the central opening formed in the central section of the lower end of the lateral wing of the ankle cuff. A connector element, such as a rivet or the like, extends through the central opening in the lower end of the lateral wing of the ankle cuff, through the central opening in the base position of the flexible lateral joint member, through the central opening in the lateral spacer-washer, and through the central opening in the central section of the upper end of the lateral wing of the foot bed member to hingedly connect the lateral wing of the foot bed member to the lateral wing of the ankle cuff.

A second embodiment of the hinged ankle brace FIGS. 1-17 is also illustrated and described. In the second embodiment of FIGS. 1-17, the outer sides of the upper ends of the medial and lateral wings of the foot bed member are outwardly curved. In the second embodiment, the outer sides of the lower ends of the medial and lateral wings of the ankle cuff are not outwardly curved or domed but are flat.

At least one strap is attached to the ankle cuff which is configured to secure a wearer's lower calf thereto.

The only difference between the hinged ankle brace of FIGS. 18-21 and the hinged ankle brace of FIGS. 1-17 is that the spacer-washers of FIGS. 18-21 are positioned at the outer sides of the flexible joint members rather than being positioned at the inner sides of the flexible joint members. The reference numerals in FIGS. 18-21 are the same reference numerals as used in the description of the hinged ankle brace of FIGS. 1-17.

It is therefore a principal object of the invention to provide an improved hinged ankle brace.

A further object of the invention is to provide a hinged ankle brace wherein the foot bed member of the ankle brace is hingedly connected to the ankle cuff of the ankle brace wherein the joint members between the foot bed members and the ankle cuff are comprised of a flexible material wherein the resistance to the hinged movement between the foot bed member and the ankle cuff increasingly resists the hinged movement of the two members as the hinged movement of the two members increases.

A further object of the invention is to provide a hinged ankle brace which not only permits a limited amount of plantarflexion and dorsiflexion movement between the ankle cuff and the foot bed member but also permits a limited amount of inversion and eversion movement therebetween.

These and other objects will be apparent to those skilled in the art.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

FIG. 12 is a plan view of one of the spacer-washers of this invention;

FIG. 13 is a side elevational view of the spacer-washer of FIG. 12;

FIG. 14 is a sectional view as seen on lines 14-14 of FIG. 12;

DESCRIPTION OF THE PREFERRED EMBODIMENT

Figure 1:
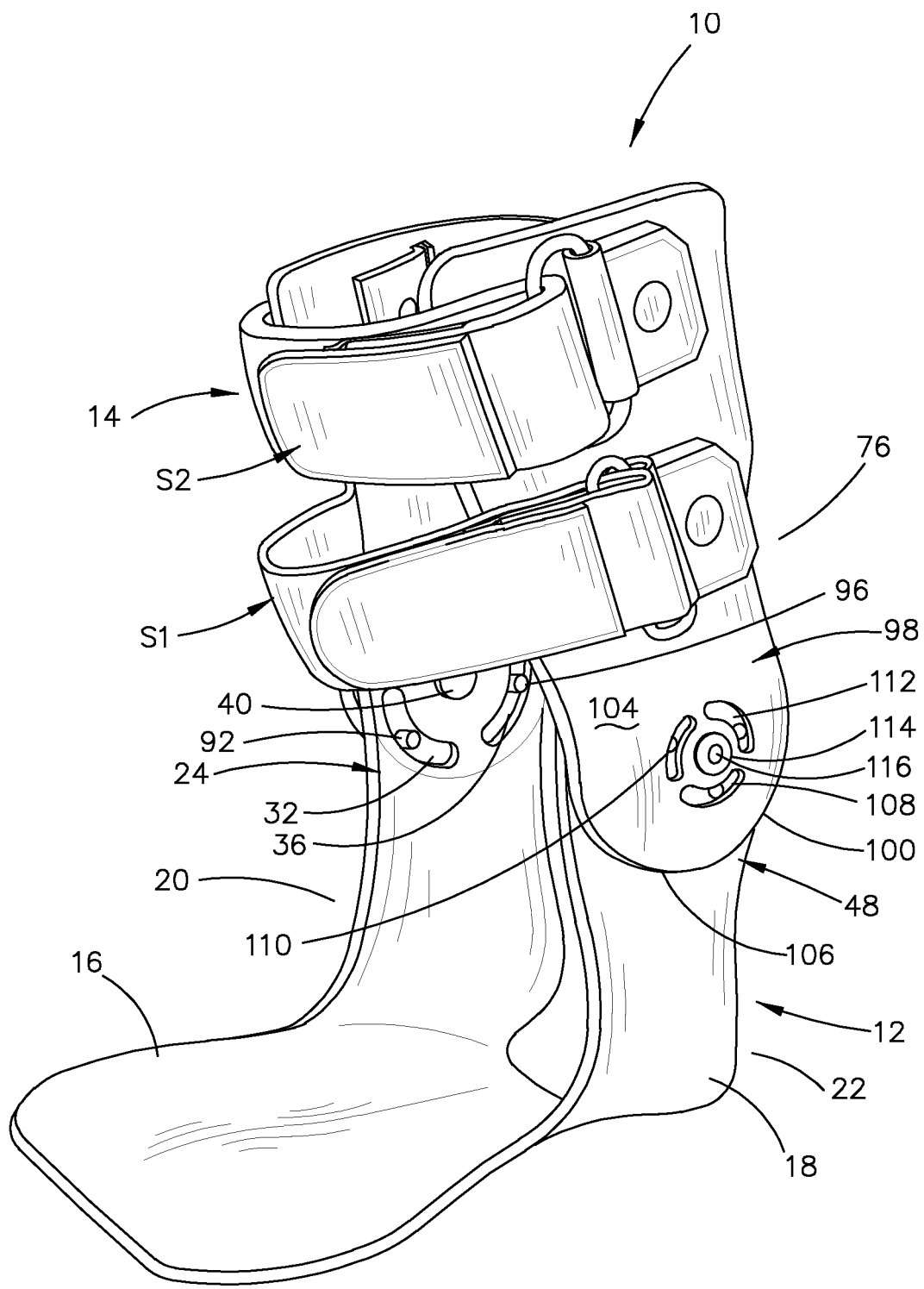
FIG. 1 is a perspective view of the ankle brace of this invention.
Figure 2:
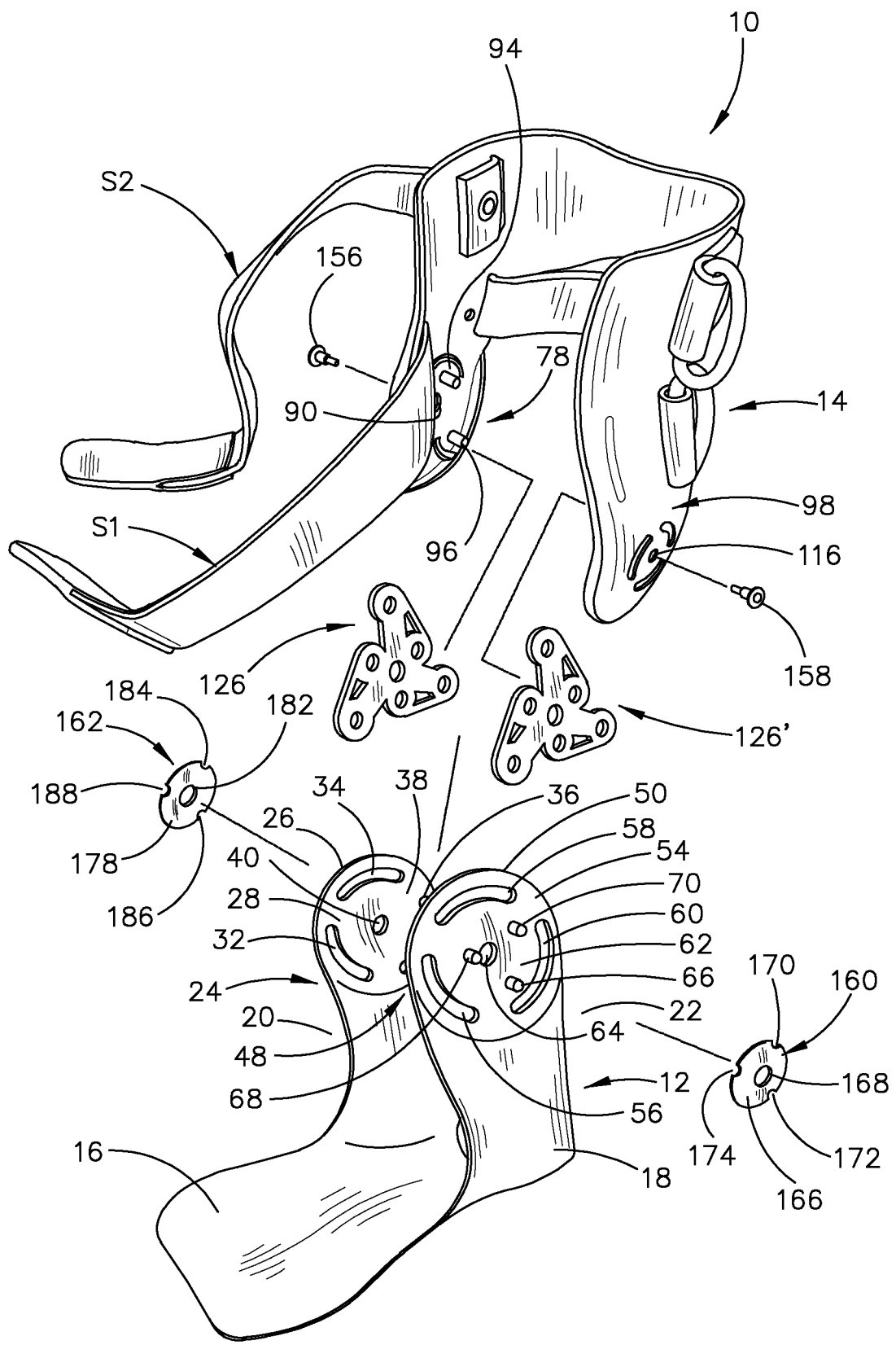
FIG. 2 is an exploded perspective view of the ankle brace of this invention.
Figure 3A:
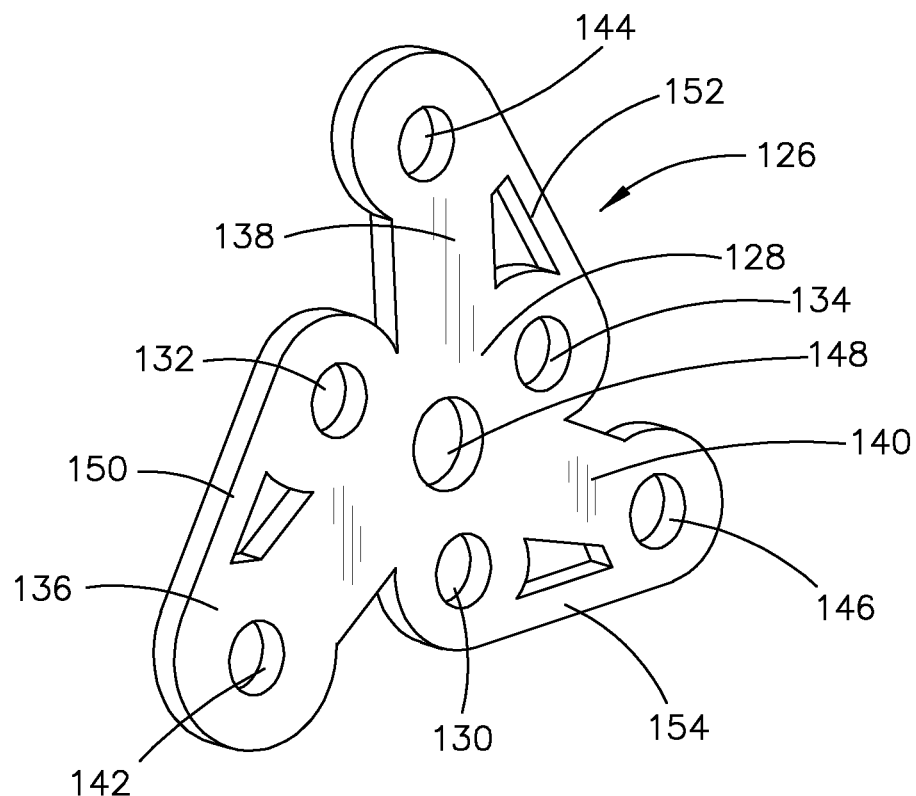
FIG. 3A is a perspective view of one of the flexible joint members of this invention.
Figure 3B:
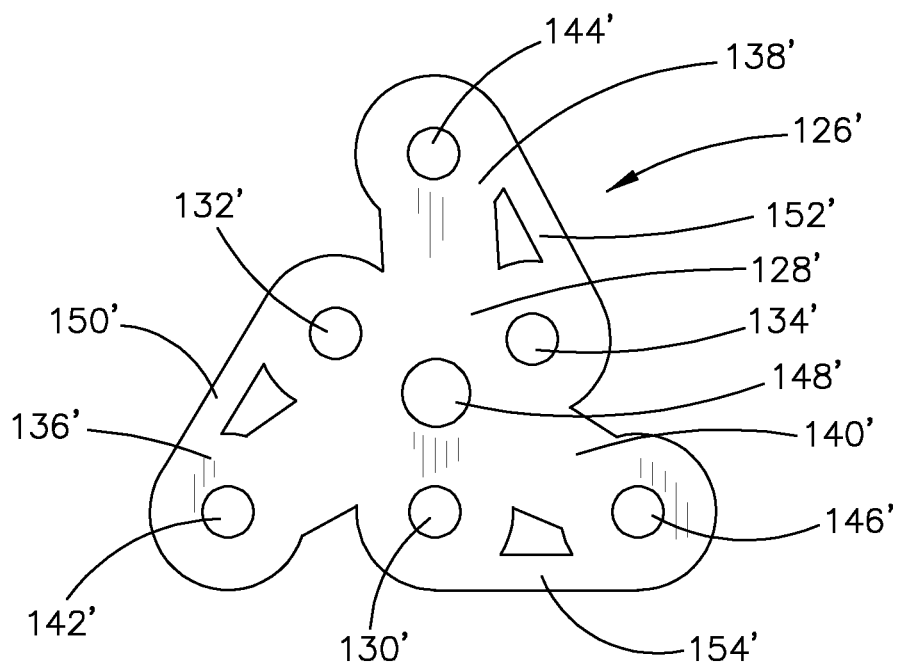
FIG. 3B is a plan view of the hinged joint member of FIG. 3A.
Figure 4:
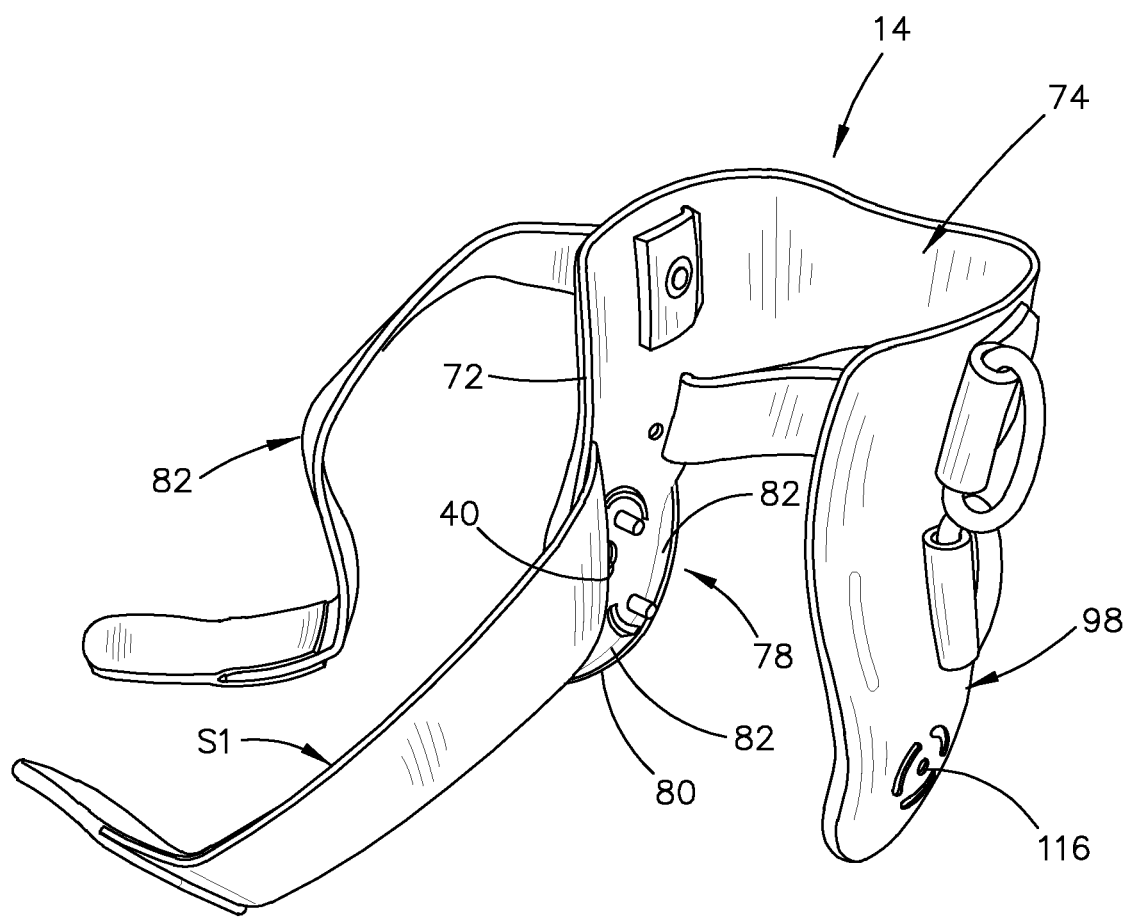
FIG. 4 is a front perspective view of the ankle cuff portion of this invention.
Figure 5:
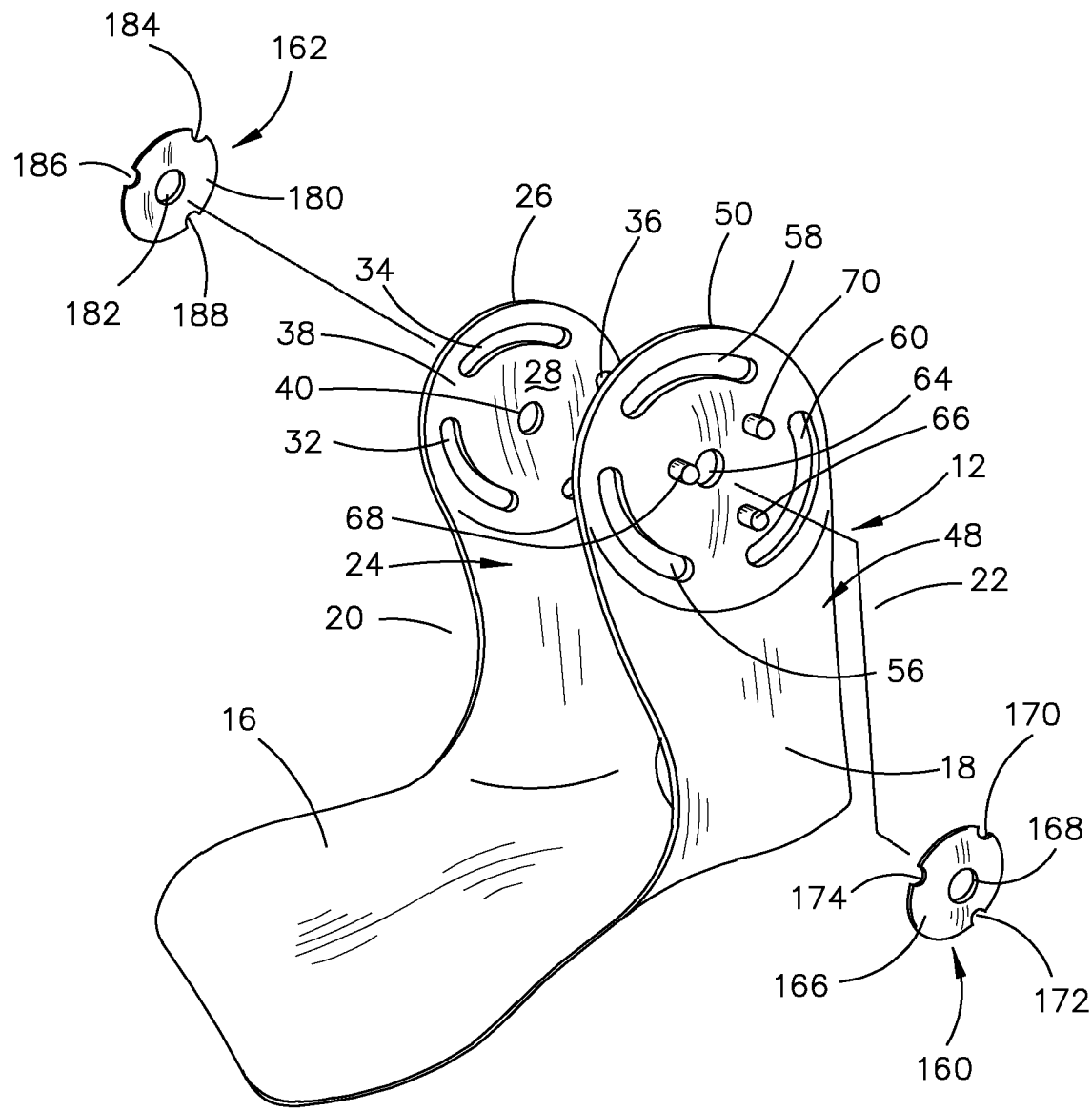
FIG. 5 is a partial exploded perspective view of the foot bed member of this invention.
Figure 5A:
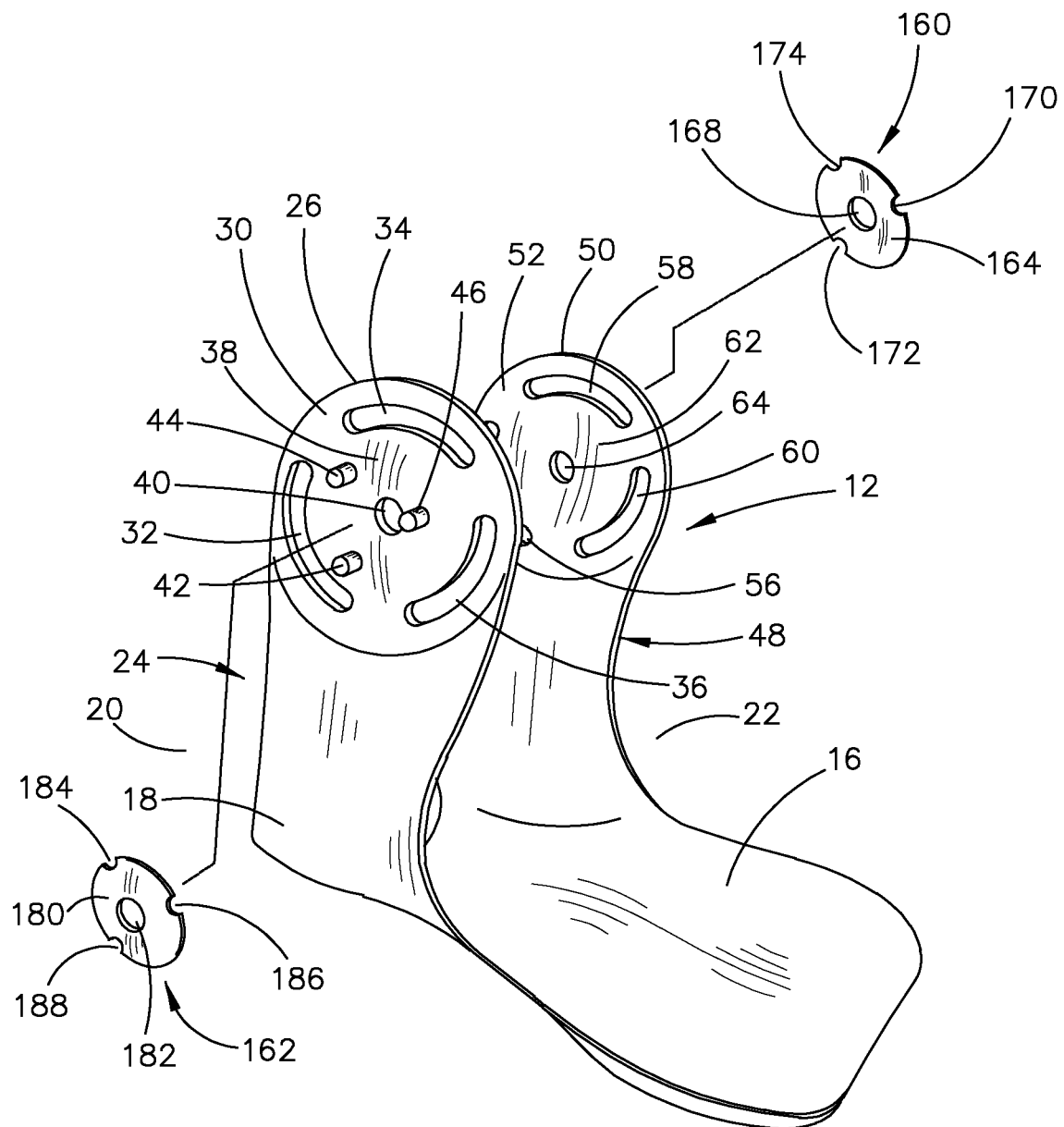
FIG. 5A is a partial exploded perspective view which is a mirror image of FIG. 5.
Figure 6:
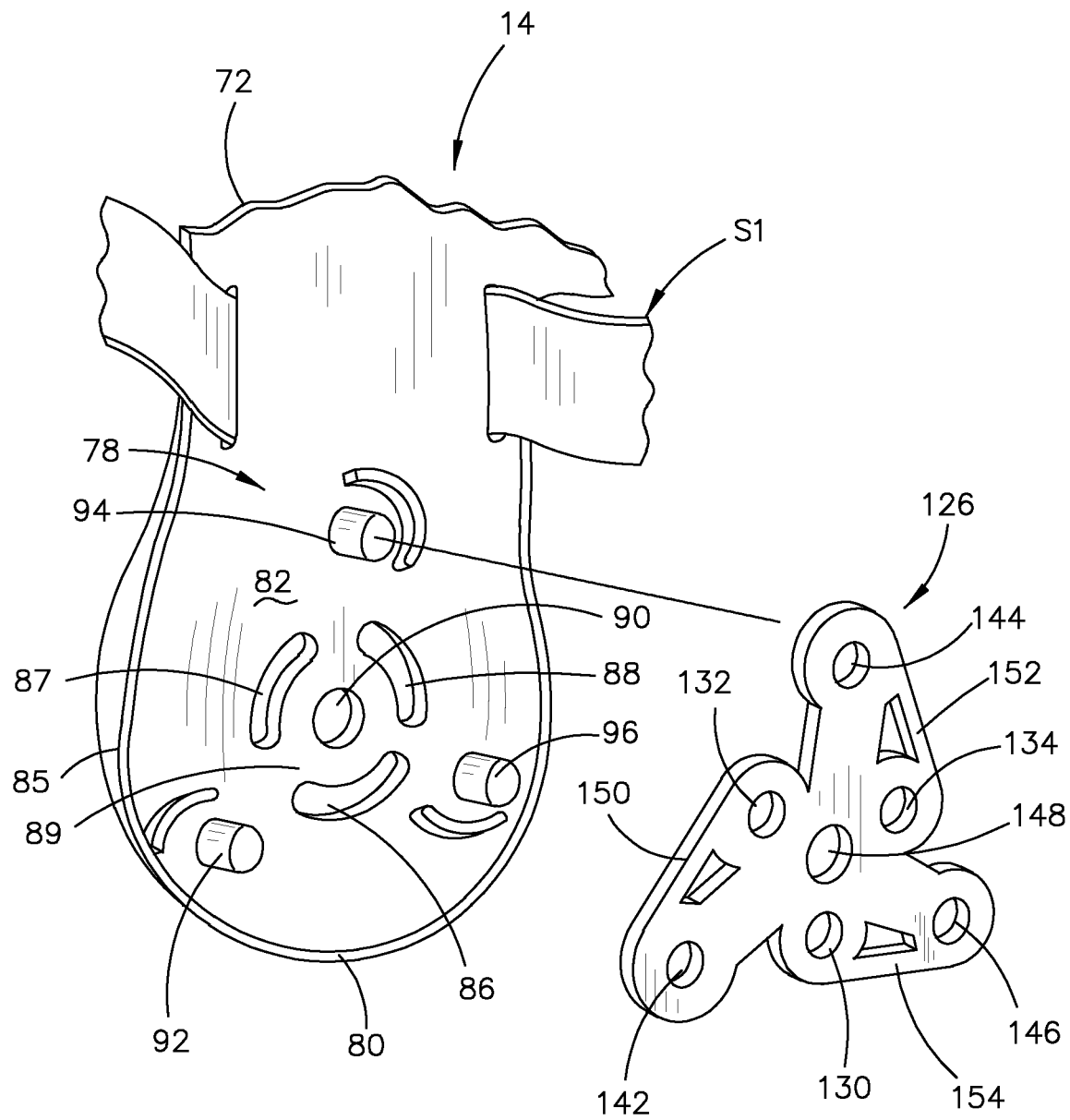
FIG. 6 is a partial exploded perspective view of the inner side of the medial wing of the ankle cuff of this invention and the flexible medial joint member of this invention.
Figure 6A:
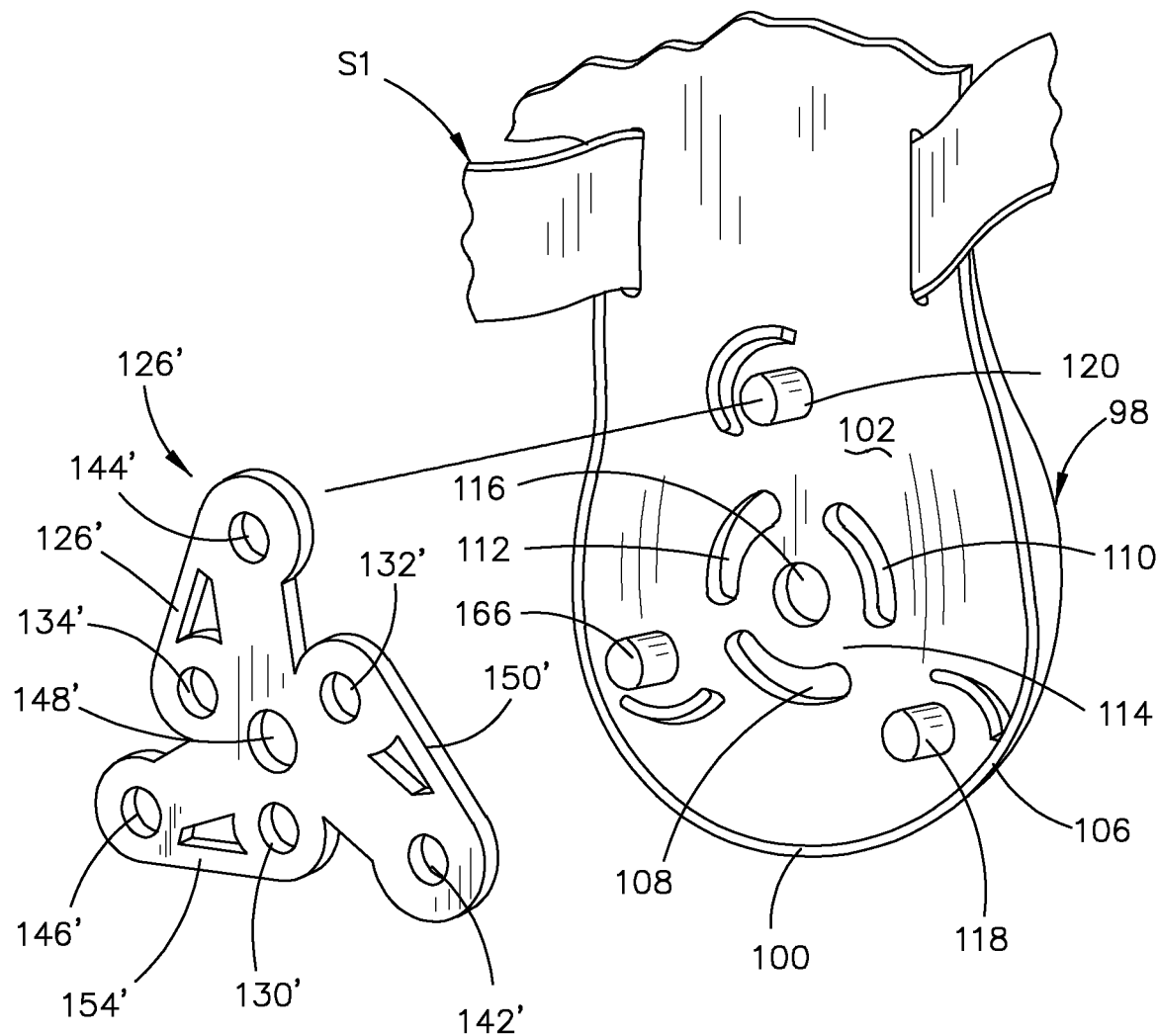
FIG. 6A is a partial exploded perspective view of the inner side of the lateral wing of the ankle cuff of this invention and the flexible lateral joint member of this invention.
Figure 7:
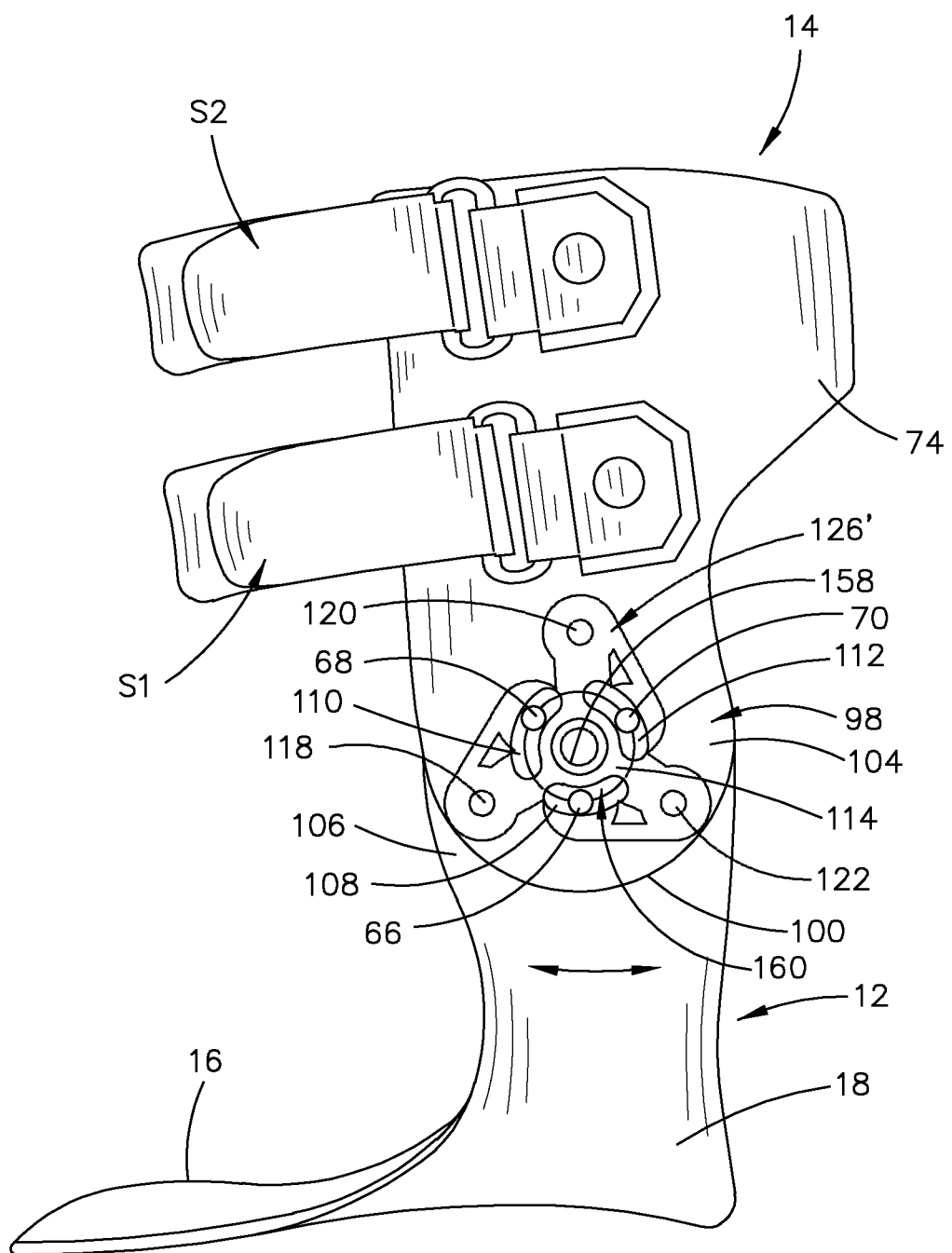
FIG. 7 is a side view of the lateral side of this invention with the flexible lateral joint member thereof being shown in broken lines.
Figure 8:
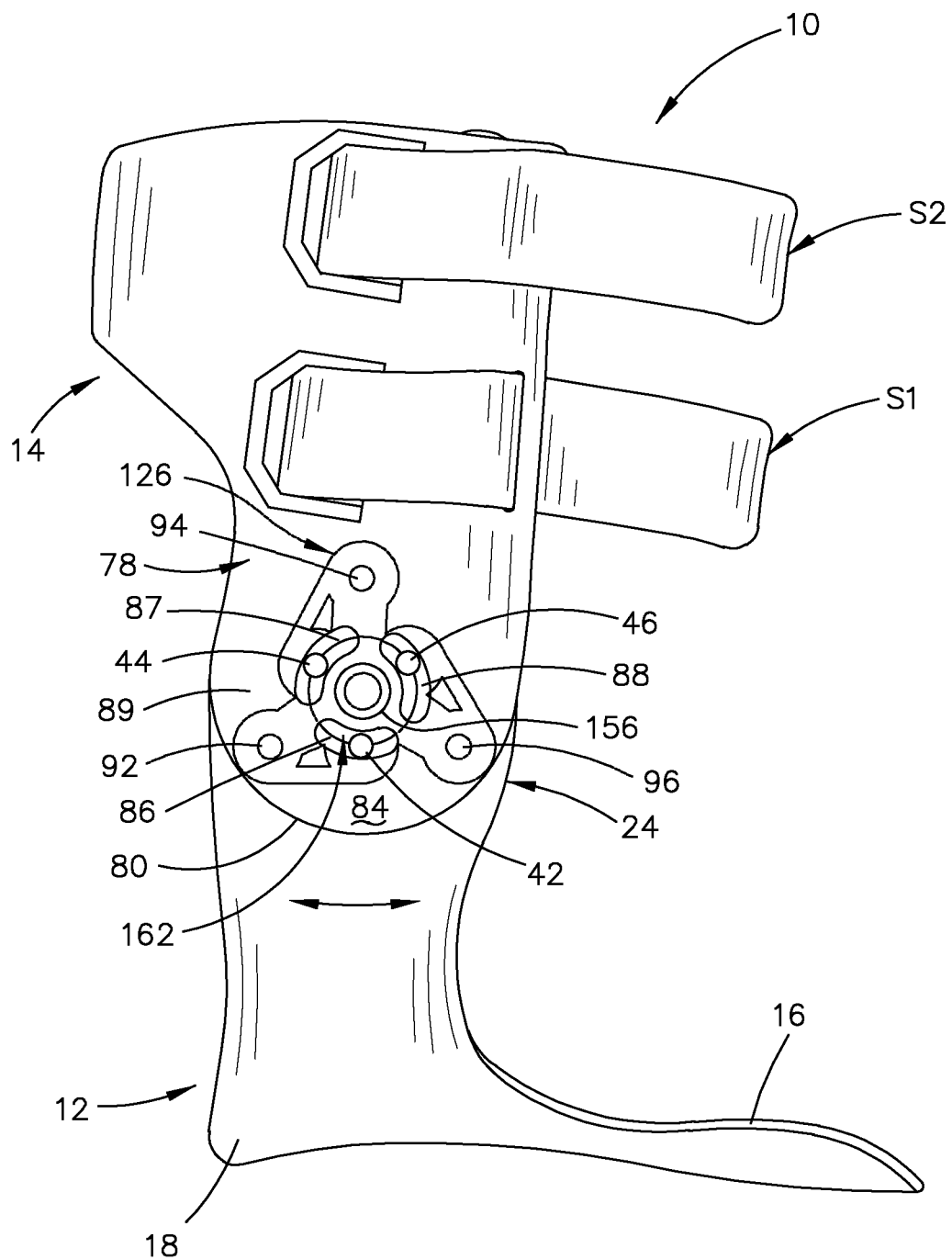
FIG. 8 is a side view of the medial side of the ankle brace of this invention with the flexible medial joint member thereof being shown in broken lines.
Figure 9:
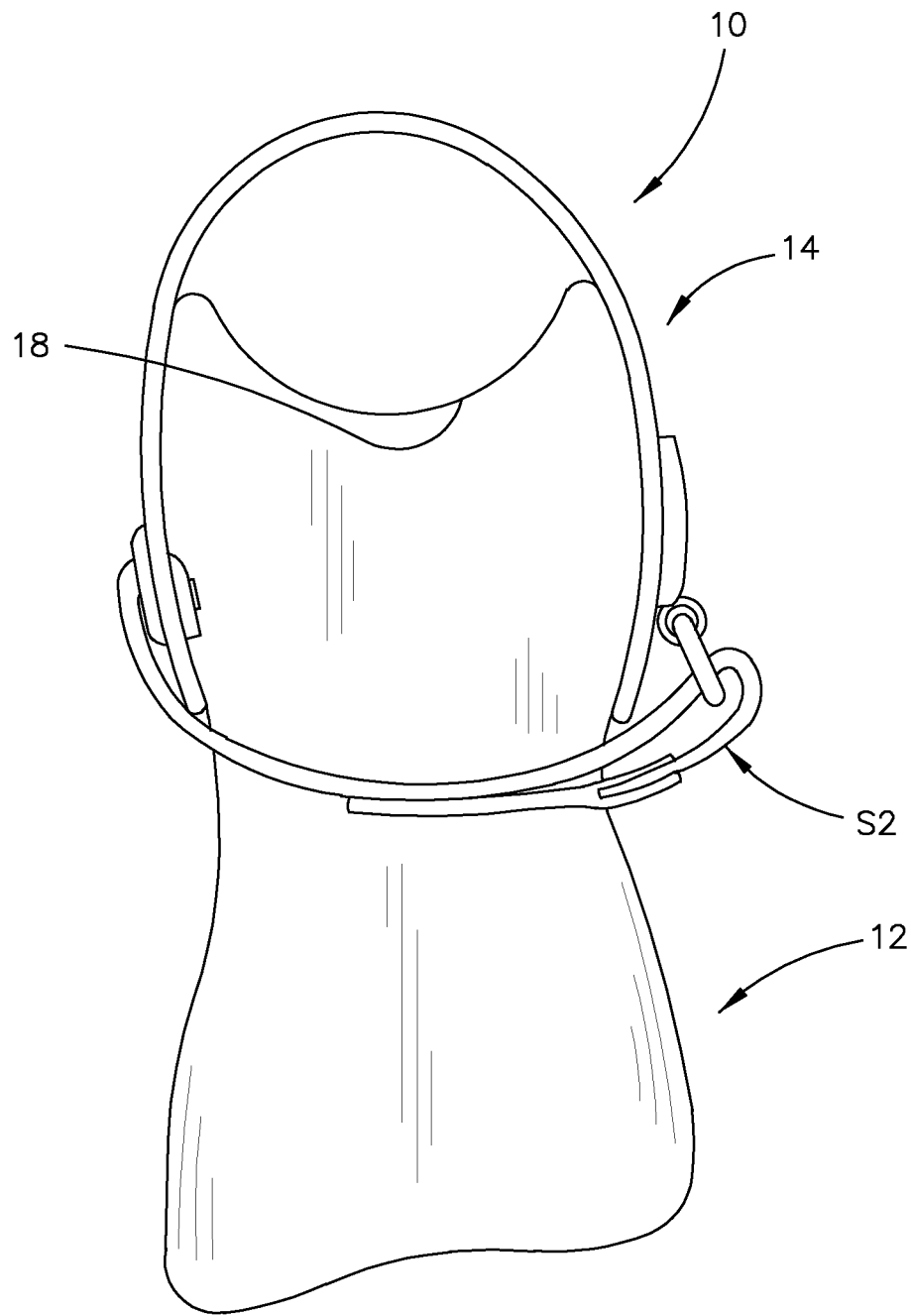
FIG. 9 is a top view of the ankle brace of this invention.
Figure 10:
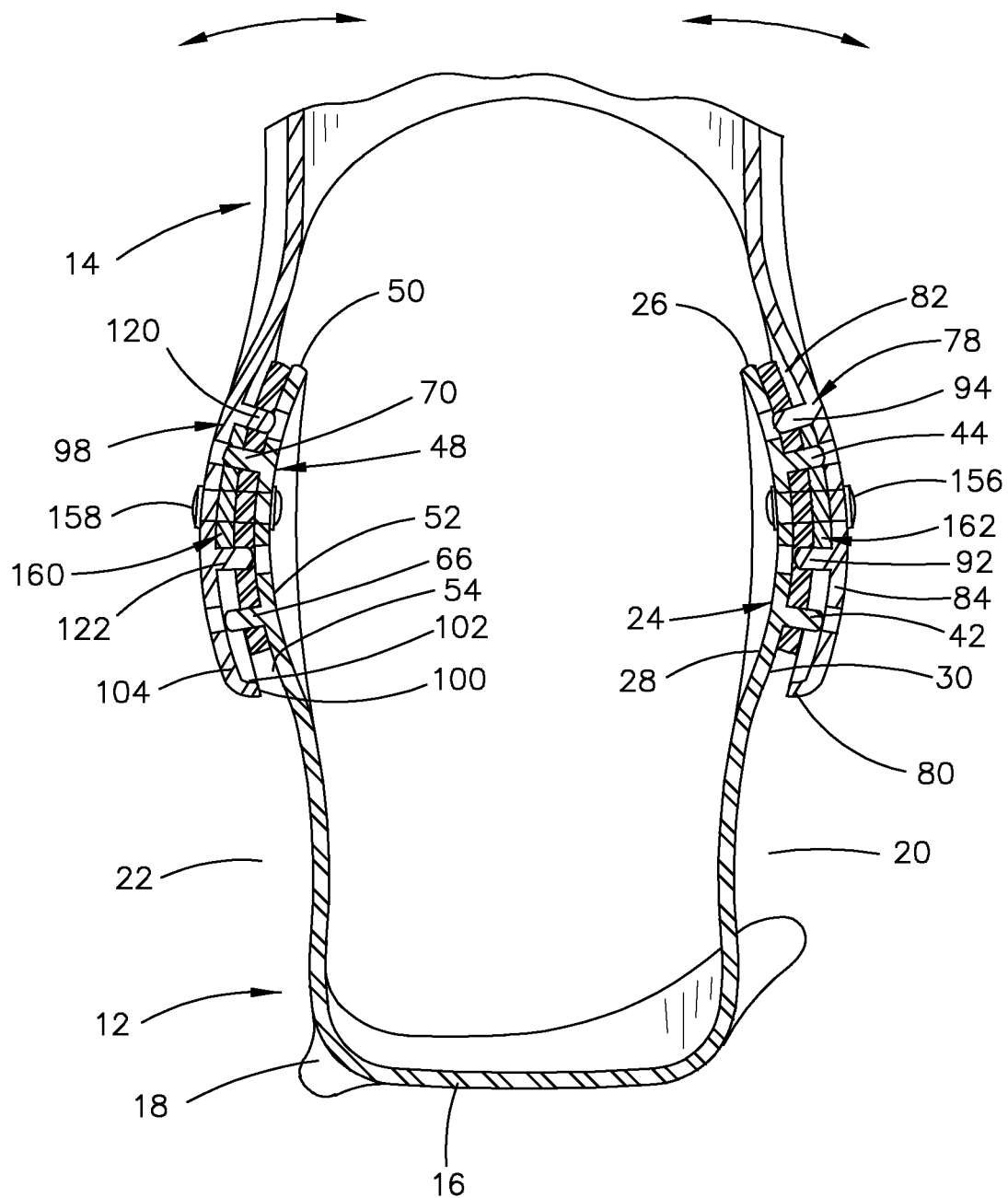
FIG. 10 is a partial sectional view of the ankle brace of this invention.
Figure 11:
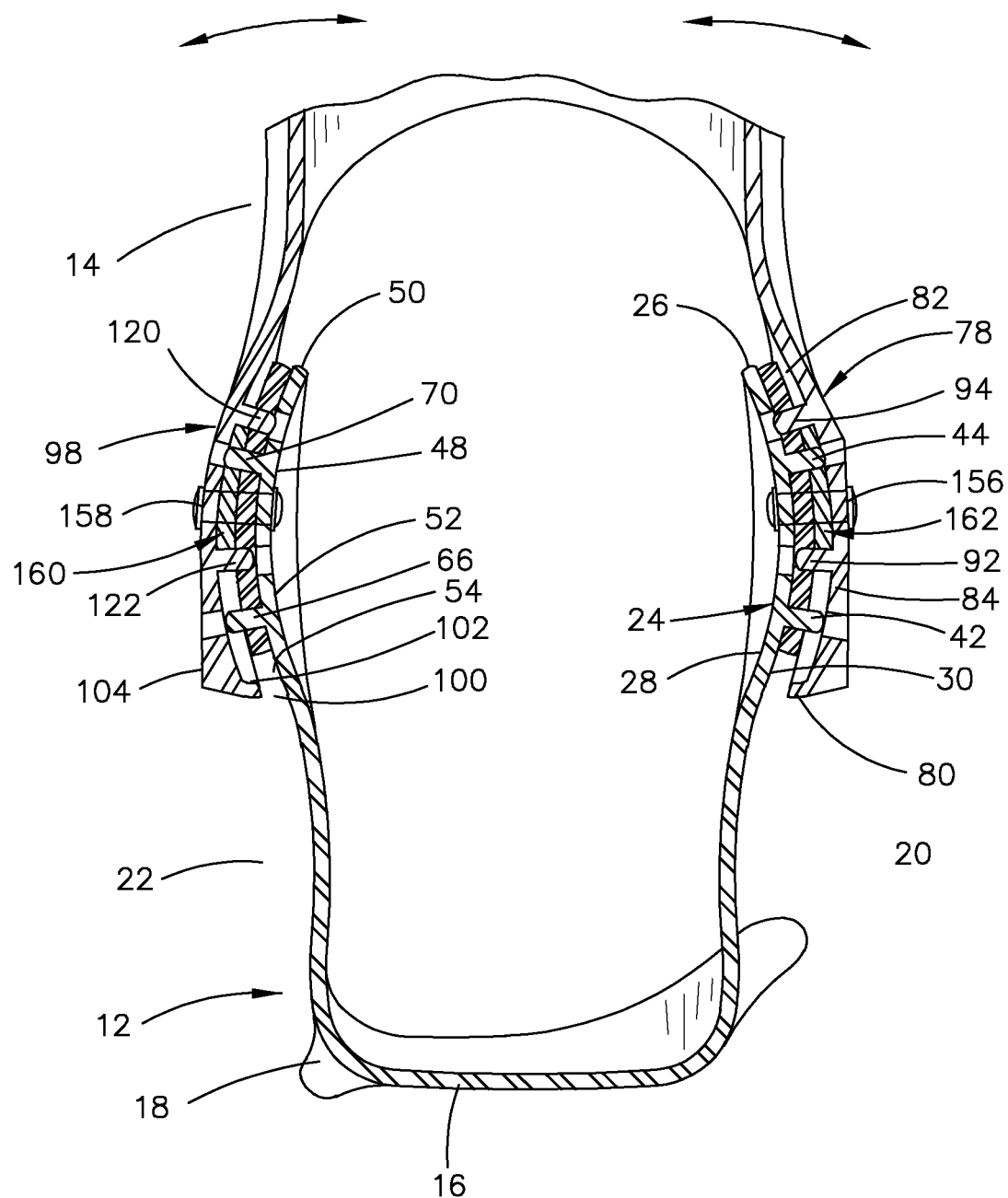
FIG. 11 is a partial sectional view of a second embodiment of the ankle brace of this invention.
Figures 15, 16:
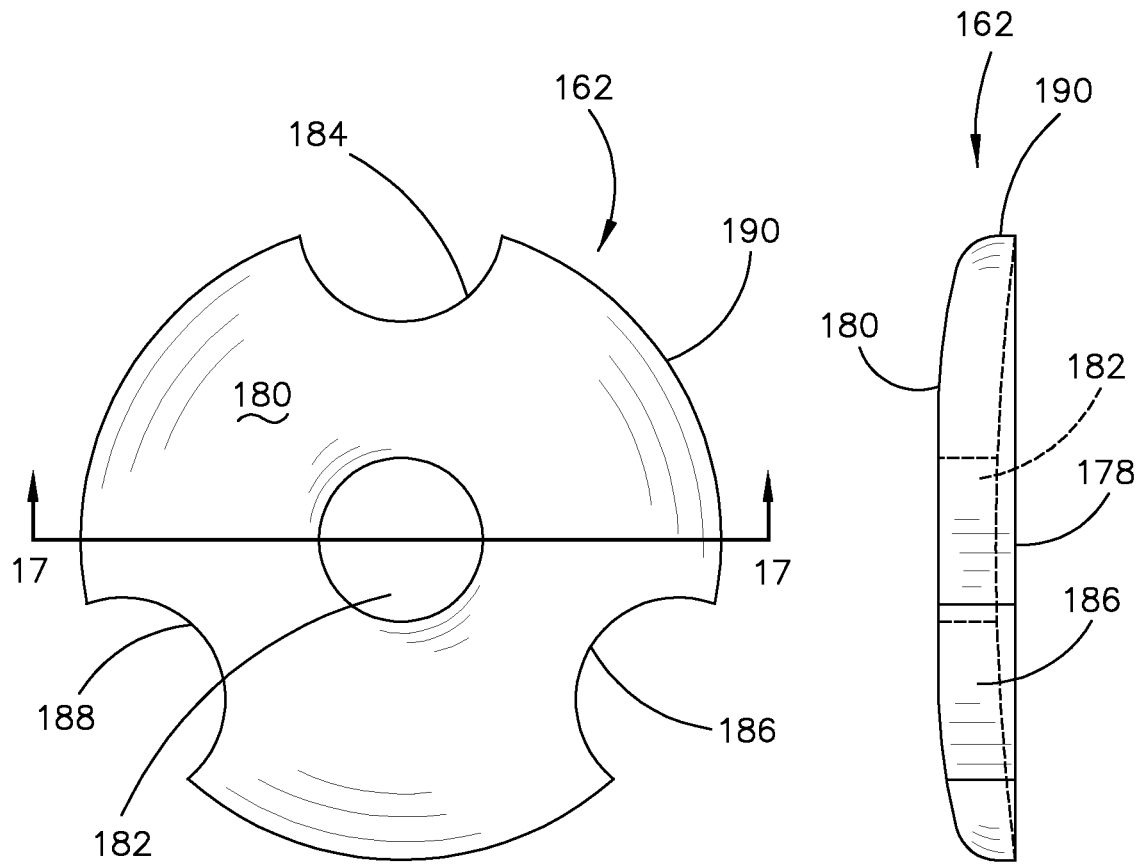
FIG. 15 is a plan view of the other spacer-washer of this invention.
FIG. 16 is a side elevational view of the spacer-washer of FIG. 15.
Figure 17:
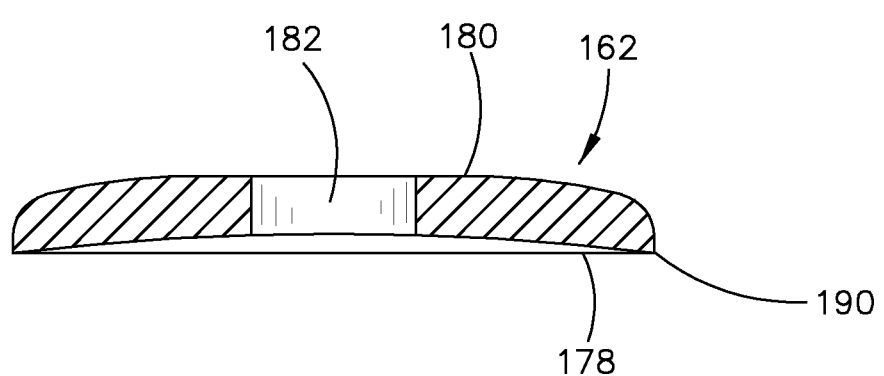
FIG. 17 is a sectional view as seen on lines 17-17 of FIG. 15.

Embodiments are described more fully below with reference to the accompanying figures, which form a part hereof and show, by way of illustration, specific exemplary embodiments. These embodiments are disclosed in sufficient detail to enable those skilled in the art to practice the invention. However, embodiments may be implemented in many different forms and should not be construed as being limited to the embodiments set forth herein. The following detailed description is, therefore, not to be taken in a limiting sense in that the scope of the present invention is defined only by the appended claims.

The hinged ankle brace of the invention of the co-pending patent application Ser. No. 17/323,318 is designated by the reference numeral 10. The description of the hinged ankle brace of FIGS. 1-17 thereof will now be described. Ankle brace 10 generally includes a foot bed member 12 and an ankle cuff 14 which are hingedly connected as will be described in detail hereinafter. The general shape of the foot bed member and the ankle cuff may vary. Ankle brace 10 will be described as being configured to be used with the left ankle and leg of a wearer. It should be understood that the ankle brace 10 could also be used to protect the right ankle of the wearer. The terms medial and lateral will apply to the left ankle brace with those terms being reversed for a right ankle brace. The brace 10 could also be easily designed to be a universal ankle brace suitable for use on either the right or left ankles.

Foot bed member 12 includes a foot plate 16 which is configured to underlie at least a portion of a foot of a wearer. Food pad member 12 also includes a heel portion 18 which is configured to receive a heel of the wearer. Foot bed member 12 will be described as having a medial side 20 and a lateral side 22. A medial wing 24 extends upwardly from the medial side 20 of the foot bed member 12. Medial wing 24 has a generally semi-circular upper end 26 with an inner side 28 and an outer side 30. The generally semi-circular upper end 26 of medial wing 24 has three radially spaced-apart and curved slots 32, 34 and 36 formed therein. The generally semi-circular upper end 26 of medial wing 24 has a central portion 38 which has a central opening 40 formed therein. Central portion 36 has three radially spaced-apart pin members 42, 44 and 46 extending outwardly therefrom. The pin members 42, 44 and 46 preferably have blunt outer ends.

The inner side 28 of the upper end 26 of medial wing 24 is outwardly curved as seen in the drawings. The outer side 30 of the upper end 26 of medial wing 24 is outwardly curved or domed as seen in the drawings.

A lateral wing 48 extends upwardly from the lateral side 22 of the foot bed member 12. Lateral wing 48 has a generally semi-circular upper end 50 with an inner side 52 and an outer side 54. The generally semi-circular upper end 50 of lateral wing 48 has three radially spaced-apart and curved slots 56, 58 and 60 formed therein. The general semi-circular upper end 50 of lateral wing 48 has a central portion 62 which has a central opening 64 formed therein. Central portion 62 has three radially spaced-apart pin members 66, 68 and 70 extending outwardly therefrom. The outer ends of pin members 66, 68 and 70 are preferably blunt. The inner side 52 of the upper end 50 of lateral wing 48 is outwardly curved as seen in the drawings. The outer side 54 of the upper end 50 of lateral wing 48 is outwardly curved or domed as seen in the drawings.

Ankle cuff 14 is designed to partially extend around the lower calf or leg of a person. Ankle cuff 14 includes a medial portion 72, a back portion 74 and a lateral portion 76. A medial wing 78 extends downwardly from the lower end of medial portion 72 and has a generally semi-circular lower end 80. Lower end 80 has an inner side 82 and an outer side 84. Preferably, medial wing 78 of ankle cuff 14 has an inwardly extending edge 85.

The lower end 80 of medial wing 78 of ankle cuff 14 has three radially spaced-apart and curved slots 86, 87 and 88 formed therein. The lower end 80 of medial wing 78 of ankle cuff 14 has a central portion 89 which has a central opening 90 formed therein. The inner side 82 of medial wing 78 has three radially spaced-apart pin members 92, 94 and 96 extending inwardly therefrom. Preferably, the inner ends of the pin members 92, 94 and 96 are blunt. The inner side 82 of medial wing 78 is outwardly curved. The outer side 84 of medial wing 78 is outwardly curved or domed as seen in the drawings.

A lateral wing 98 extends downwardly from the lower end of lateral portion 76 of ankle cuff 14 and has a generally semi-circular lower end 100. Lower end 100 has an inner side 102 and an outer side 104. Preferably, the lower end 100 of lateral wing 98 has an inwardly extending edge 106. The lower end 100 of lateral wing 98 has three radially spaced-apart and curved slots 108, 110 and 112 formed therein. The lower end 100 of lateral wing 98 has a central portion 114 which has a central opening 116 formed therein. The inner side 102 of lateral wing 98 has three radially spaced-apart pin members 118, 120 and 122 which extend inwardly therefrom. Preferably, the inner ends of the pin members 118, 120 and 122 are blunt. The inner side 102 of lateral wing 98 is outwardly curved. The outer side 104 of lateral wing 98 is outwardly curved or domed.

The reference number 126 refers to a flat flexible medial joint member which hingedly connects medial wing 24 of foot bed member 12 to medial wing 78 of ankle cuff 14. Joint member 126 is comprised of a flexible polyurethane material or other similar material. Joint member 126 is flat and has an inner side and an outer side. Joint member 126 includes a central base portion 128 which had radially spaced-apart pin openings 130, 132 and 134 formed therein. Support arms 136, 138 and 140 extend outwardly from base portion 128 in a radially spaced-apart manner. Arms 136, 138 and 140 have pin openings 142, 144 and 146 formed in the outer ends thereof. Base portion 128 includes a central opening 148 formed therein. Joint member 126 includes a rib 150 which extends between base portion 128 and support arm 136. A rib 152 extends between base portion 128 and support arm 138, and a rib 154 extends between base portion 128 and support arm 140.

Joint member 126 is positioned at the inner side of lower end 80 of medial wing 78 of ankle cuff 14 as seen in the drawings. When so positioned, the pin members 92, 94 and 96, which extend inwardly from the inner side 82 of lower end 80 of medial wing 78, extend into the pin openings 130, 132 and 134 in the outer ends of the support arms 136, 138 and 140 respectively. When so positioned, the inner ends of the pin members 92, 94 and 96 protrude from joint member 126.

The reference numeral 126' refers to a flat flexible lateral joint member which hingedly connects lateral wing 48 of foot bed member 12 to lateral wing 98 of ankle cuff 14. Joint member 126' is comprised of a flexible polyurethane material or other similar material. Joint member 126' is flat and has an inner side and an outer side. Joint member 126' includes a central base portion 128' which has radially spaced-apart pin openings 130', 132' and 134' formed therein. Support arms 136', 138' and 140' extend outwardly from base portion 128' in a radially spaced-apart manner. Arms 136', 138' and 140' have pin openings 142', 144' and 146' formed in the outer ends thereof. Base portion 128' includes a central opening 148' formed therein. Joint member 126' includes a rib 150' which extends between base portion 128' and support arm 136', a rib 152' which extends between base portion 126' and support arm 138', and a rib 154' which extends between base portion 128' and support arm 140'.

Joint member 126' is positioned at the inner side 102 of lower end 100 of lateral wing 98 of ankle cuff 14 as seen in the drawings. When so positioned, the pin members 118, 120 and 122, which extend inwardly from the inner side 102 of lower end 104 of lateral wing 98, extend into the pin openings 130', 132', and 134' in the outer ends of the support arms 136', 138', and 140' respectively. When so positioned, the inner ends of the pin members 92', 94' and 96' protrude from joint member 126'.

In the co-pending published application, a rivet 156 extends through opening 90 in medial wing 78 of ankle cuff 14, through opening 148 in medial joint 126, and through opening 40 in medial wing 24 of foot bed member 12. In the co-pending application, a rivet 158 extends through opening 116 in lateral wing 98 of ankle cuff 14, through opening 148' in lateral joint 126', and through opening 64 in lateral wing 48 of foot bed member 12. The rivets 156 and 158 hingedly connect foot bed member 12 to ankle cuff 14.

The hinged ankle brace 10 discussed hereinabove is the same hinged ankle brace shown and described in application Ser. No. 17/130,338 filed Dec. 22, 2020, entitled A HINGED ANKLE BRACE which is a Continuation-in-Part Application of application Ser. No. 16/367,929 filed Dec. 2, 2016, entitled A HINGED ANKLE BRACE. The hinged ankle brace of the invention of patent application Ser. No. 17/323, 318 includes a pair of spacer-washers 160 and 162 which are identical.

Lateral spacer-washer 160 is disc-shaped and has an inner side 164 and an outer side 166. As seen, the inner side 164 thereof is curved inwardly which is the preferred shape. The outer side 166 of spacer-washer 160 is outwardly curved.

However, the outer side 166 could be flat in some situations. Medial spacer-washer 160 has a central opening 168 formed therein. Spacer-washer 160 has three semi-circular openings 170, 172 and 174 extending into the periphery 176 thereof. Medial spacer-washer 162 is disc-shaped and has an inner side 178 and an outer side 180. As seen, the inner side 178 is curved inwardly which is the preferred shape. The outer side 180 of spacer-washer 162 is outwardly curved. However, the outer side 180 could be flat is some situations. Spacer-washer 162 has a central opening 182 formed therein. Spacer-washer 162 has three semi-circular opening 184, 186 and 188 extending into the periphery 180 thereof.

Lateral spacer-washer 160 is positioned at the outer side of the upper end 50 of lateral wing 48 so as to be positioned between the pin members 66, 68 and 70 with the pin members 66, 68 and 70 thereof being received in the semi-circular openings 172, 174 and 170 thereof respectively. The central opening 168 of lateral spacer-washer 160 registers with the central opening 64 of lateral wing 48.

Pin, bolt or rivet 156 extends inwardly through opening 90 in medial wing 78 of ankle cuff 14, through opening 148 in medial joint member 126, through central opening 182 in medial spacer-washer 162, and through opening 40 in wing member 24 of foot bed member 12.

Medial spacer-washer 162 is positioned at the outer side of the upper end 26 of medial wing 24 of foot bed member 12 so as to be positioned between the pin members 42, 44 and 46 with the pin members being received in the semi-circular openings 188, 184 and 186 of medial spacer-washer 160 respectively. The central opening 182 in spacer-washer 160 registers with the opening 40 of medial wing 24.

Pin bolt rivet 158 extends inwardly through opening 116 in lateral wing member 98, through central opening 148' of lateral joint member 126', through central opening 168 in lateral spacer-washer 160, and through the opening 64 in lateral wing 48 of foot bed member 12.

The flexible joint members of FIGS. 1-17 create greater resistance to hinged movement of the foot bed member and the ankle cuff thereof as the two members hingedly move to a greater degree with respect to one another in a plantar-flexion and dorsiflexion direction. Each of the flexible joint members 126 and 126' are designed to create more resistance the further it moves but eventually butts up against the inner portion thereof to stop further movement thereof. The inner sides of the lower ends of the medial and lateral wings of the ankle cuff are outwardly curved and the outer sides of the upper ends of the medial and lateral wings of the foot bed member are outwardly curved and will permit a limited amount of inversion and eversion movement between the foot bed member and the ankle cuff. The medial spacer-washer and the lateral spacer-washer also permit an additional amount of eversion and inversion movement between the foot bed member and the ankle cuff. The spacer-washers will provide the necessary eversion and inversion movement if the medial and lateral wings are outwardly curved. The spacer-washers may have flat outer and inner sides but preferably have slightly curved or domed outer sides. The spacer-washers are preferably comprised of plastic or aluminum. The thicknesses of the spacer-washers 160 and 162 may be varied to vary the mount of inversion/eversion permitted thereby. As seen in the drawings, the ankle brace of this invention is preloaded with some dorsiflexion. However, the ankle brace may be easily preloaded with plantar-flexion.

Figure 18:
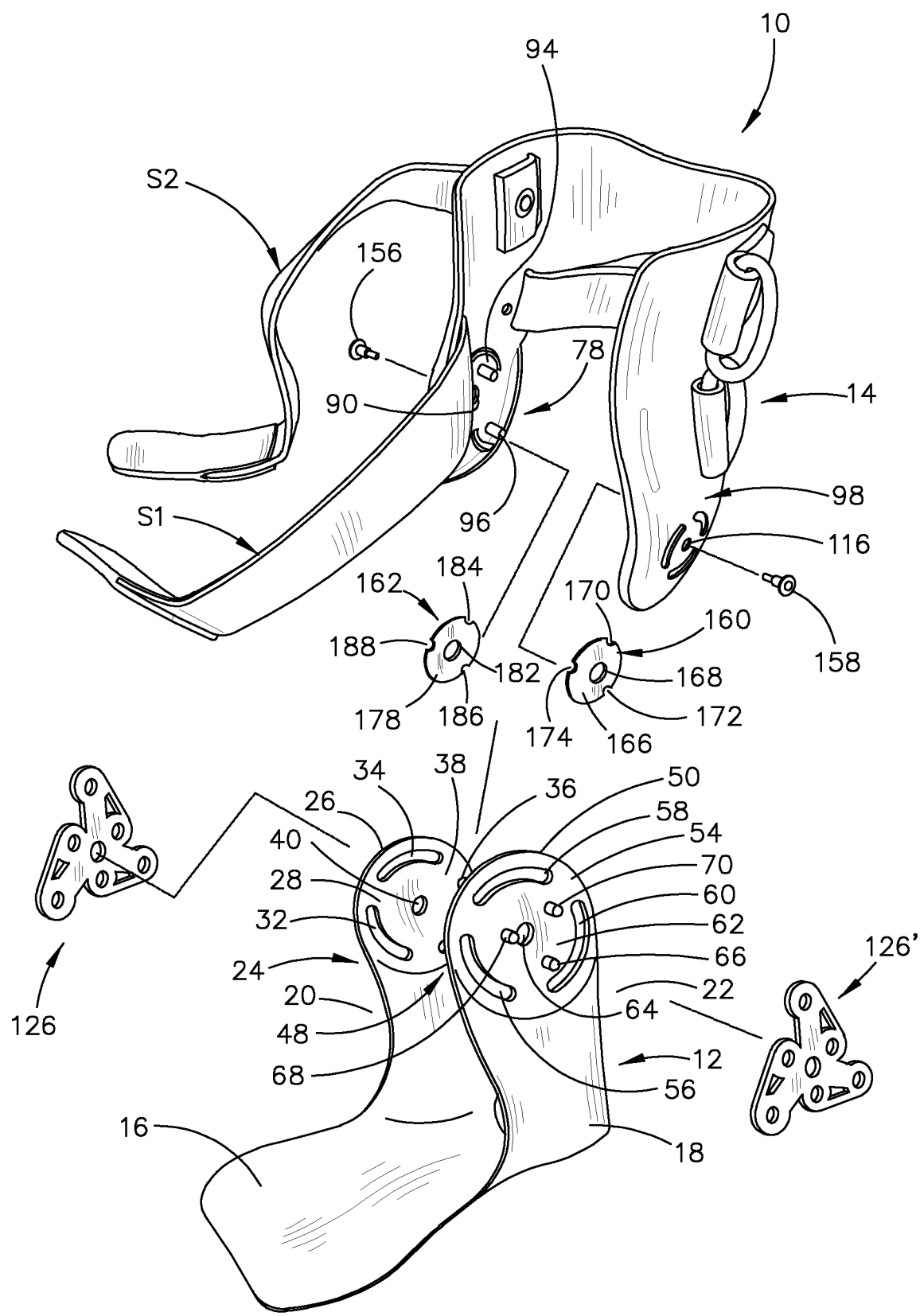
FIG. 18 is an exploded perspective view of the ankle brace similar to FIG. 2 except that the spacer-washers are positioned at the outer sides of the flexible joint members.
Figure 19:
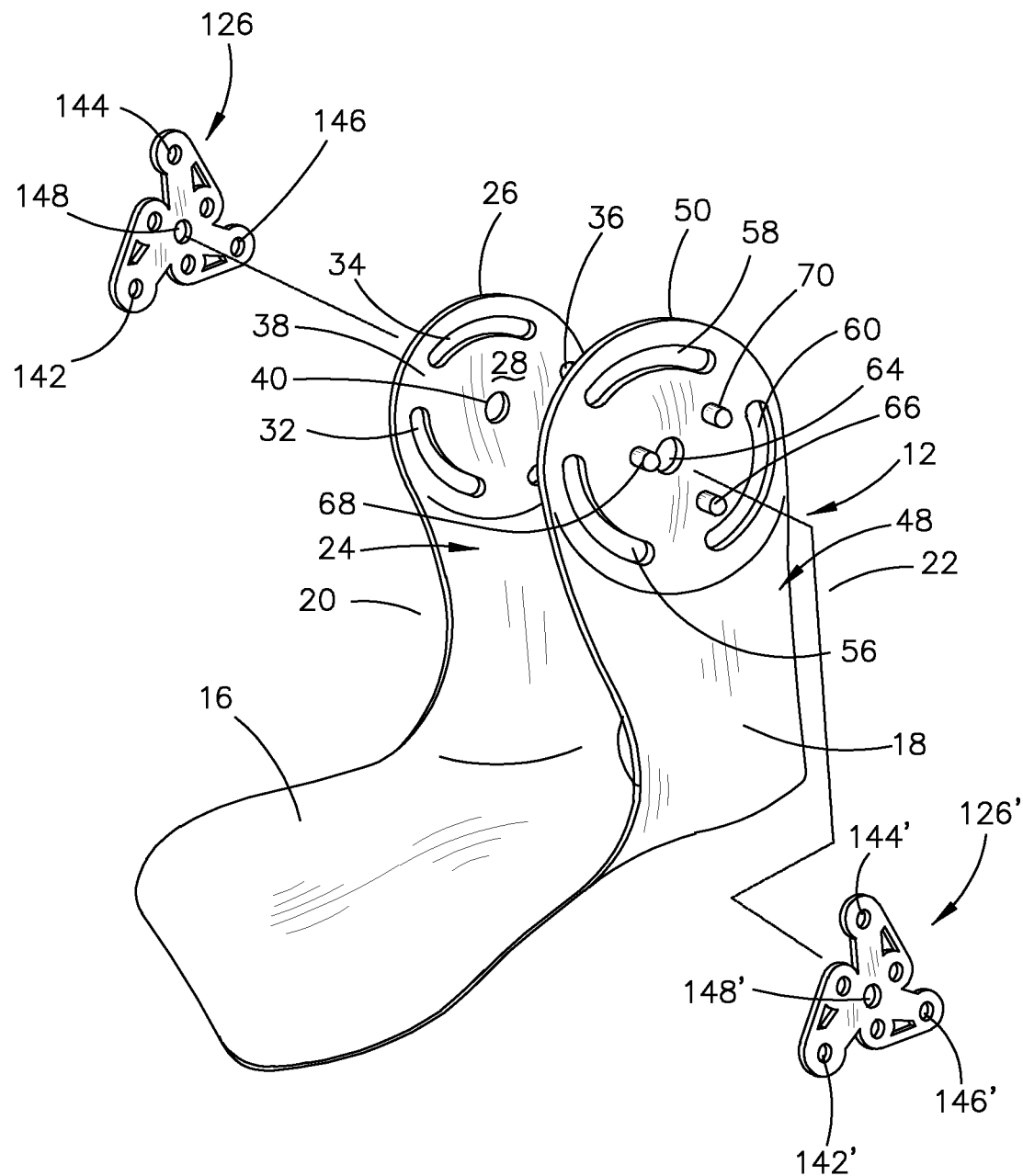
FIG. 19 is a partial exploded perspective view of the ankle brace of FIG. 18.
Figure 20:
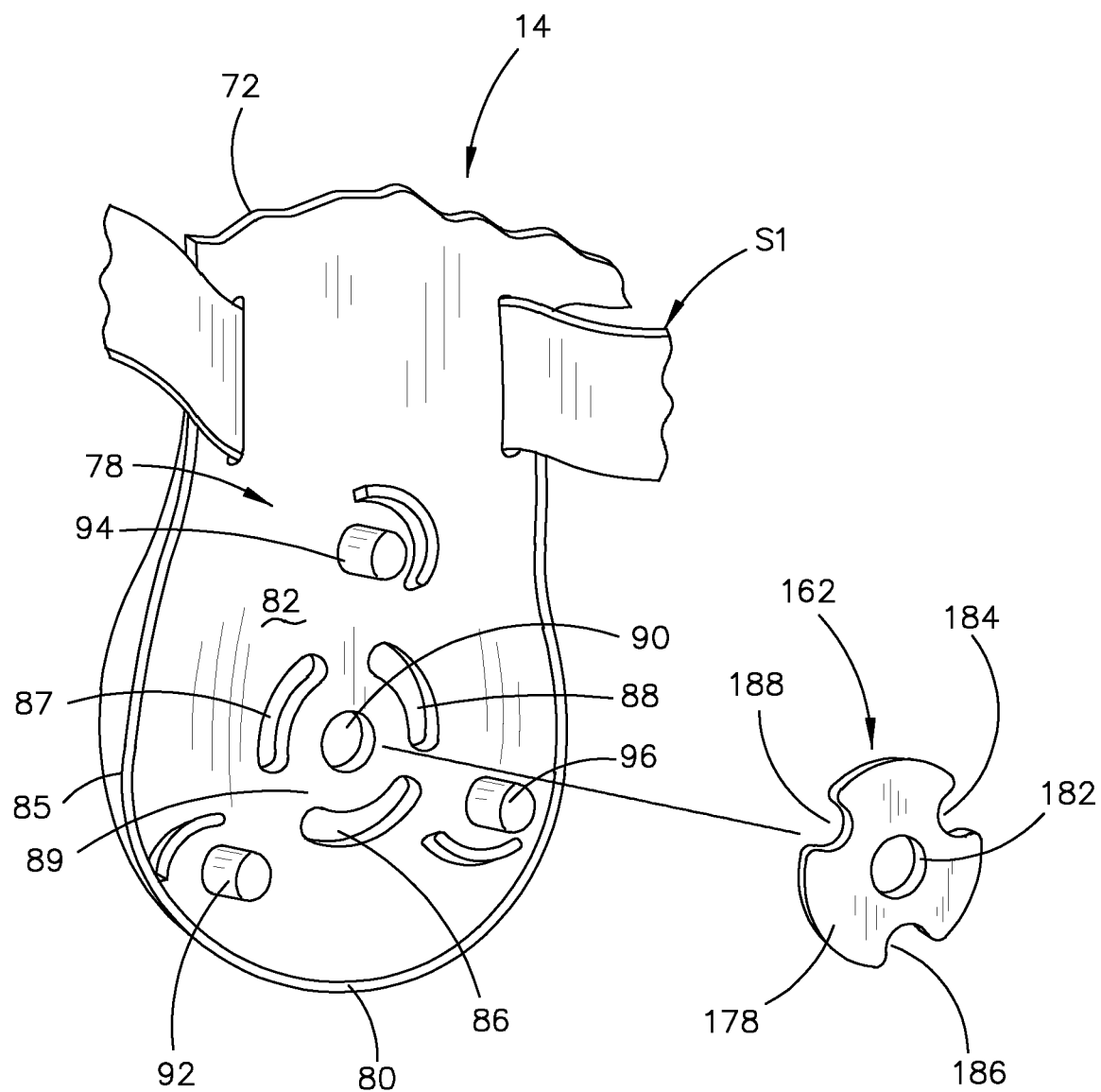
FIG. 20 is a partial exploded perspective view of the inner side of the medial wing of the ankle cuff of FIG. 18 and the spacer-washer associated therewith.
Figure 21:
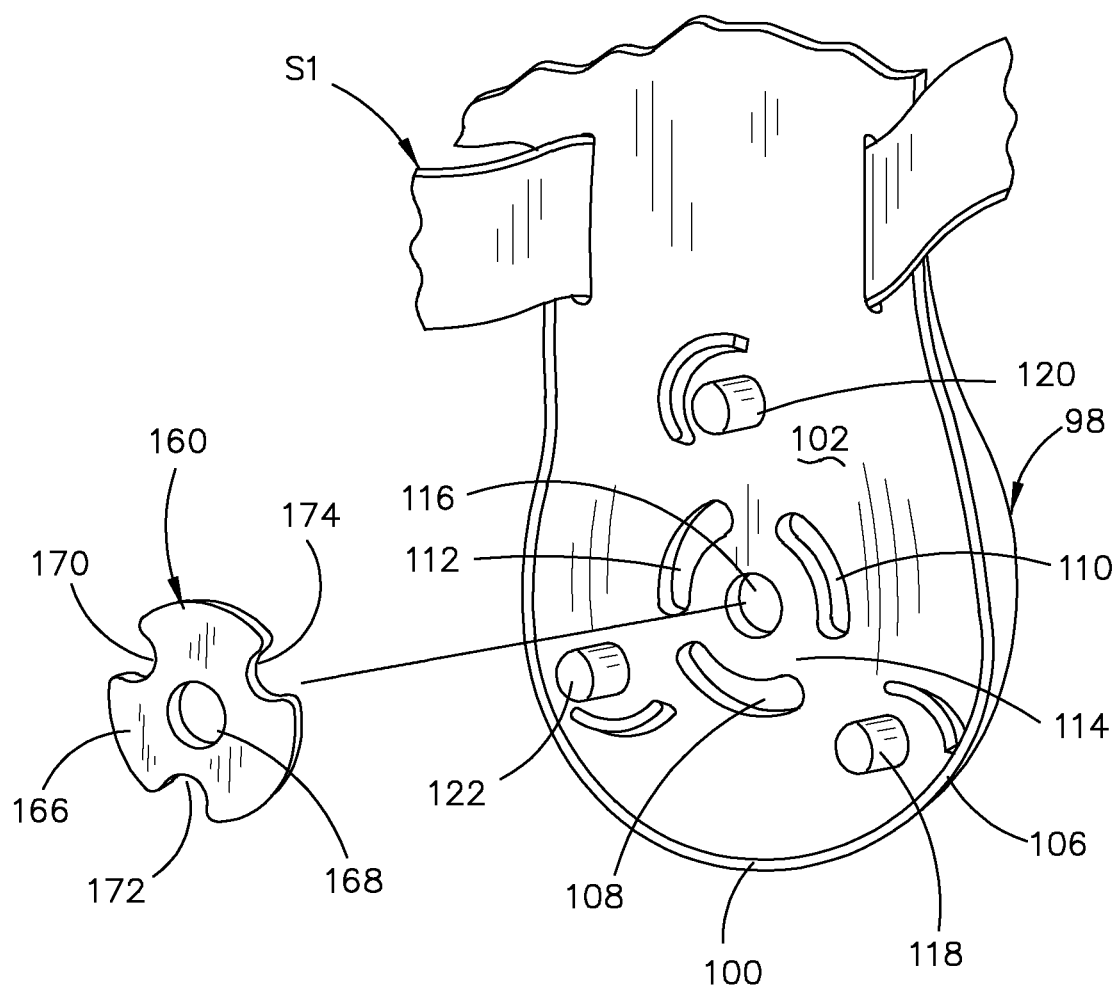
FIG. 21 is a partial exploded perspective view of the inner side of the lateral wing of the ankle cuff of this invention and the spacer-washer associated therewith.

The only differences between the hinged ankle brace of FIGS. 1-17 and the ankle brace of FIGS. 18-20 are that the spacer-washer 162 is positioned on the outer side of the flexible joint member 126 and the spacer-washer 160 is positioned on the outer side of the flexible joint member 126'. This is made possible as will now be described. The flexible medial joint member 126 is positioned on the outer side of the medial wing 20 with the flexible joint member 126 being mounted on the pin members 42, 44 and 46. The flexible joint member 126' is positioned on the outer side of the lateral wing 22 with the flexible joint member 126' being mounted on the pin members 66, 68 and 70. The spacer-washer 162 is mounted between the pin members 92, 94 and 96 of the medial wing 78 of ankle cuff 78. The spacer-washer 160 is mounted between the pin members 118, 120 and 122 of lateral wing 98 of ankle cuff 14. When assembled, the spacer-washers 160 and 162 are positioned at the outer sides of flexible joint members 126' and 126 respectively.

The spacer-washers 160 and 162 permit an additional amount of eversion and inversion movement between the foot bed member and the ankle cuff.

Thus it can be seen that the invention accomplishes at least all of its stated objectives.

Although the invention has been described in language that is specific to certain structures and methodological steps, it is to be understood that the invention defined in the appended claims is not necessarily limited to the specific structures and/or steps described. Rather, the specific aspects and steps are described as forms of implementing the claimed invention. Since many embodiments of the invention can be practiced without departing from the spirit and scope of the invention, the invention resides in the claims hereinafter appended.

I claim:

1. A hinged ankle brace, comprising:
   a foot bed member including a foot plate configured to underlie at least a portion of a foot of a wearer and a portion configured to receive a heel of the wearer;
   said foot bed member having a medial side and a lateral side;
   a medial wing extending upwardly from said medial side of said foot bed member;
   said medial wing of said foot bed member having a generally semi-circular upper end with inner and outer sides;
   said upper end of said medial wing of said foot bed member having:
   (a) first, second and third radially spaced-apart and curved slots formed therein;
   (b) a central section positioned between said first, second and third slots;
   (c) a central opening formed in said central section thereof; and
   (d) first, second and third radially spaced-apart pin members extending outwardly from said outer side of said central section thereof;
   said outer side of said upper end of said medial wing of said foot bed member being outwardly curved;
   said inner side of said upper end of said medial wing of said foot bed member being outwardly curved;
   a lateral wing extending upwardly from said lateral side of said foot bed member;
   said lateral wing of said foot bed member having a generally semi-circular upper end with inner and outer sides;
   said upper end of said lateral wing of said foot bed member having:
   (a) first, second and third radially spaced-apart and curved slots formed therein;

(b) a central section positioned between said first, second and third slots;
(c) a central opening formed in said central section; and
(d) first, second and third radially spaced-apart pin members extending outwardly from said central section thereof;

said outer side of said upper end of said lateral wing of said foot bed member being outwardly curved;
said inner side of said upper end of said lateral wing of said foot bed member being outwardly curved;
an ankle cuff, having upper and lower ends, including a leg supporting portion configured to extend at least partially around a posterior side of a lower leg of a wearer;
said ankle cuff having a medial side and a lateral side;
said ankle cuff having a medial wing extending downwardly from said medial side of said ankle cuff;
said medial wing of said ankle cuff having a generally semi-circular lower end with inner and outer sides;
said lower end of said medial wing of said ankle cuff having:
  (a) first, second and third radially spaced-apart and curved slots formed therein;
  (b) a central section positioned between said first, second and third slots thereof;
  (c) a central opening formed in said central section thereof; and
  (d) first, second and third radially spaced-apart pin members extending inwardly from said inner side thereof;
said outer side of said lower end of said medial wing of said ankle cuff being outwardly curved;
said inner side of said lower end of said medial wing of said ankle cuff being outwardly curved;
said inner side of said lower end of said medial wing of said ankle cuff being positioned outwardly of said outer side of said upper end of said medial wing of said foot bed member;
said ankle cuff having a lateral wing extending downwardly from said lateral side of said ankle cuff;
said lateral wing of said ankle cuff having a generally semi-circular lower end with inner and outer sides;
said inner side of said lower end of said lateral wing of said ankle cuff being positioned outwardly of said outer side of said upper end of said lateral wing of said foot bed member;
said lower end of said lateral wing of said ankle cuff having:
  (a) first, second and third radially spaced-apart and curved slots formed therein;
  (b) a central section positioned between said first, second and third slots thereof;
  (c) a central opening formed in said central section thereof; and
  (d) first, second and third radially spaced-apart pin members extending inwardly from said inner side of said lower end thereof;
said outer side of said lower end of said lateral wing of said ankle cuff being outwardly curved;
said inner side of said lower end of said lateral wing of said ankle cuff being outwardly curved;
a flat flexible medial joint member positioned at said outer side of said upper end of said medial wing of said foot bed member;
said flat flexible medial joint member including:
  (a) a flat base portion having an inner side and an outer side;
  (b) said flat base portion having first, second and third radially spaced-apart pin openings formed therein;
  (c) said flat base portion having a central opening formed therein;
  (d) said flat base portion having first, second and third radially spaced-apart arms extending therefrom with each of said arms having inner and outer ends;
  (e) a fourth pin opening formed in said outer end of said first arm;
  (f) a fifth pin opening formed in said outer end of said second arm;
  (g) a sixth pin opening formed in said outer end of said third arm; and
said first, second and third pin members which extend outwardly from said outer side of said upper end of said medial wing of said foot bed member extending through said first, second and third pin openings in said flat base portion of said flat flexible medial joint member respectively;
said central opening in said central section of said upper end of said medial wing of said foot bed member being aligned with said central opening of said flat base portion of said flat flexible medial joint member and being aligned with said central opening in central section of said medial wing of said ankle cuff;
said fourth, fifth and sixth pin openings in said flat flexible medial joint member being aligned with said first, second and third slots formed in said upper end of said medial wing of said foot bed member;
a disc-shaped medial spacer-washer having an inner side, an outer side, a central opening, and first, second and third radially spaced-apart semi-circular openings formed in the periphery thereof;
said disc-shaped medial spacer-washer being positioned at said outer side of said flat flexible medial joint member whereby said central opening in said medial spacer-washer registers with said central opening in said flat base portion of said flat flexible medial joint member and said central opening of said medial wing of said foot bed member and so that said first, second and third pin members which extend outwardly from said outer side of said central section of said medial wing of said foot bed member are received by said first, second and third semi-circular openings in the periphery of said medial spacer-washer;
a flat flexible lateral joint member positioned at said outer side of said upper end of said lateral wing of said foot bed member;
said flat flexible lateral joint member including:
  (a) a flat base portion having an inner side and an outer side;
  (b) said flat base portion having first, second and third radially spaced-apart pin openings formed therein;
  (c) said flat base portion having a central opening formed therein;
  (d) said flat base portion having first, second and third radially spaced-apart arms extending therefrom with each of said arms having inner and outer ends;
  (e) a fourth pin opening formed in said outer end of said first arm;
  (f) a fifth pin opening formed in said outer end of said second arm;
  (g) a sixth pin opening formed in said outer end of said third arm;
said first, second and third pin members which extend from said inner side of said lower end of said lateral wing of said ankle cuff extending through said fourth, fifth and sixth pin openings in said flat flexible lateral joint member and extending into said first, second and third slots in said upper end of said lateral wing of said foot bed member respectively;

a disc-shaped lateral spacer-washer having an inner side, an outer side, a central opening and first, second and third radially spaced-apart semi-circular openings formed in the periphery thereof;

said disc-shaped lateral spacer-washer being positioned at said outer side of said flat flexible lateral joint member whereby said central opening in said lateral spacer-washer registers with said central opening in said flat base portion of said flat flexible lateral joint member and said central opening of said lateral wing of said foot bed member and so that said first, second and third pin members which extend outwardly from said outer side of said central section of said lateral wing of said foot bed member are received by said first, second and third semi-circular openings in the periphery of said lateral spacer-washer;

and a first connector member extending through said central opening in said central section of said lower end of said medial wing of said ankle cuff, through said central opening in said medial spacer-washer, through said central opening in said flat base portion of said flat flexible medial joint member, and through said central opening in said central section of said upper end of said medial wing of said foot bed member to hingedly connect said lower end of said medial wing of said ankle cuff to said upper end of said medial wing of said foot bed member;

and a second connector member extending through said central opening in said central section of said lower end of said lateral wing of said ankle cuff, through said central opening in said lateral spacer-washer, through said central opening in said central section in said flat base portion of said flat flexible lateral joint member, and through said central opening in said central section of said upper end of said lateral wing of said foot bed portion to hingedly connect said lower end of said lateral wing of said ankle cuff to said upper end of said lateral wing of said foot bed member;

said flat flexible medial joint member and said flat lateral joint member yieldably resisting plantarflexion and dorsiflexion hinged movement between said foot bed member and said ankle cuff with said flat flexible medial and said flat lateral joint members increasingly yieldably resisting the plantarflexion and dorsiflexion hinged movement between said foot bed member and said ankle cuff as the plantarflexion and dorsiflexion hinged movement therebetween increases;

said outwardly curved outer side of said upper end of said medial wing of said foot bed member and said outwardly curved inner side of said lower end of said medial wing of said ankle cuff permitting a limited amount of inversion and eversion movement therebetween;

said outwardly curved outer side of said upper end of said lateral wing of said foot bed member and said outwardly curved inner side of said lateral wing of said ankle cuff permitting a limited amount of inversion and eversion movement;

said medial spacer-washer and said lateral spacer-washer permitting an additional amount of eversion and inversion movement between said foot bed member and said ankle cuff; and at least one strap attached to said ankle cuff configured to secure a wearer's lower leg thereto.

2. A hinged ankle brace, comprising:

a foot bed member including a foot plate configured to underlie at least a portion of a foot of a wearer and a portion configured to receive a heel of the wearer;

said foot bed member having a medial side and a lateral side;

a medial wing extending upwardly from said medial side of said foot bed member;

said medial wing of said foot bed member having a generally semi-circular upper end with inner and outer sides;

said upper end of said medial wing of said foot bed member having:
(a) first, second and third radially spaced-apart and curved slots formed therein;
(b) a central section positioned between said first, second and third slots;
(c) a central opening formed in said central section thereof; and
(d) first, second and third radially spaced-apart pin members extending outwardly from said outer side of said central section thereof;

a lateral wing extending upwardly from said lateral side of said foot bed member;

said lateral wing of said foot bed member having a generally semi-circular upper end with inner and outer sides;

said upper end of said lateral wing of said foot bed member having:
(a) first, second and third radially spaced-apart and curved slots formed therein;
(b) a central section positioned between said first, second and third slots;
(c) a central opening formed in said central section; and
(d) first, second and third radially spaced-apart pin members extending outwardly from said central section thereof;

an ankle cuff, having upper and lower ends, including a leg supporting portion configured to extend at least partially around a posterior side of a lower leg of a wearer;

said ankle cuff having a medial side and a lateral side;

said ankle cuff having a medial wing extending downwardly from said medial side of said ankle cuff;

said medial wing of said ankle cuff having a generally semi-circular lower end with inner and outer sides;

said lower end of said medial wing of said ankle cuff having:
(a) first, second and third radially spaced-apart and curved slots formed therein;
(b) a central section positioned between said first, second and third slots thereof;
(c) a central opening formed in said central section thereof; and
(d) first, second and third radially spaced-apart pin members extending inwardly from said inner side thereof;

said inner side of said lower end of said medial wing of said ankle cuff being positioned outwardly of said outer side of said upper end of said medial wing of said foot bed member;

said ankle cuff having a lateral wing extending downwardly from said lateral side of said ankle cuff;

said lateral wing of said ankle cuff having a generally semi-circular lower end with inner and outer sides;

said inner side of said lower end of said lateral wing of said ankle cuff being positioned outwardly of said outer side of said upper end of said lateral wing of said foot bed member;

said lower end of said lateral wing of said ankle cuff having:
  (a) first, second and third radially spaced-apart and curved slots formed therein;
  (b) a central section positioned between said first, second and third slots thereof;
  (c) a central opening formed in said central section thereof; and
  (d) first, second and third radially spaced-apart pin members extending inwardly from said inner side of said lower end thereof;

a flat flexible medial joint member positioned at said inner side of said lower end of said medial wing of said ankle cuff;

said flat flexible medial joint member including:
  (a) a flat base portion having an inner side and an outer side;
  (b) said flat base portion having first, second and third radially spaced-apart pin openings formed therein;
  (c) said flat base portion having a central opening formed therein;
  (d) said flat base portion having first, second and third radially spaced-apart arms extending therefrom with each of said arms having inner and outer ends;
  (e) a fourth pin opening formed in said outer end of said first arm;
  (f) a fifth pin opening formed in said outer end of said second arm;
  (g) a sixth pin opening formed in said outer end of said third arm; and said first, second and third pin members which extend outwardly from said outer side of said upper end of said medial wing of said foot bed member extending through said first, second and third pin openings in said flat base portion of said flat flexible medial joint member respectively;

said central opening in said central section of said upper end of said medial wing of said foot bed member being aligned with said central opening of said flat base portion of said flat flexible medial joint member and being aligned with said central opening in central section of said medial wing of said ankle cuff;

said fourth, fifth and sixth pin openings in said flat flexible medial joint member being aligned with said first, second and third slots formed in said upper end of said medial wing of said foot bed member;

a disc-shaped medial spacer-washer having an inner side, an outer side, a central opening, and first, second and third radially spaced-apart semi-circular openings formed in the periphery thereof;

said disc-shaped medial spacer-washer being positioned at said outer side of said flat flexible medial joint member whereby said central opening in said medial spacer-washer registers with said central opening in said flat base portion of said flat flexible medial joint member and said central opening of said medial wing of said foot bed member and so that said first, second and third pin members which extend outwardly from said outer side of said central section of said medial wing of said foot bed member are received by said first, second and third semi-circular openings in the periphery of said medial spacer-washer;

a flat flexible lateral joint member positioned at said outer side of said upper end of said lateral wing of said foot bed member;

said flat flexible lateral joint member including:
  (a) a flat base portion having an inner side and an outer side;
  (b) said flat base portion having first, second and third radially spaced-apart pin openings formed therein;
  (c) said flat base portion having a central opening formed therein;
  (d) said flat base portion having first, second and third radially spaced-apart arms extending therefrom with each of said arms having inner and outer ends;
  (e) a fourth pin opening formed in said outer end of said first arm;
  (f) a fifth pin opening formed in said outer end of said second arm;
  (g) a sixth pin opening formed in said outer end of said third arm;

said first, second and third pin members which extend from said inner side of said lower end of said lateral wing of said ankle cuff extending through said fourth, fifth and sixth pin openings in said flat flexible lateral joint member and extending into said first, second and third slots in said upper end of said lateral wing of said foot bed member respectively;

a disc-shaped lateral spacer-washer having an inner side, an outer side, a central opening and first, second and third radially spaced-apart semi-circular openings formed in the periphery thereof;

said disc-shaped lateral spacer-washer being positioned at said outer side of said flat flexible lateral joint member whereby said central opening in said lateral spacer-washer registers with said central opening in said flat base portion of said flat flexible lateral joint member and said central opening of said lateral wing of said foot bed member and so that said first, second and third pin members which extend outwardly from said outer side of said central section of said lateral wing of said foot bed member are received by said first, second and third semi-circular openings in the periphery of said lateral spacer-washer;

and a first connector member extending through said central opening in said central section of said lower end of said medial wing of said ankle cuff, through said central opening in said medial spacer-washer, through said central opening in said flat base portion of said flat flexible medial joint member, and through said central opening in said central section of said upper end of said medial wing of said foot bed member to hingedly connect said lower end of said medial wing of said ankle cuff to said upper end of said medial wing of said foot bed member;

and a second connector member extending through said central opening in said central section of said lower end of said lateral wing of said ankle cuff, through said central opening in said lateral spacer-washer, through said central opening in said central section in said flat base portion of said flat flexible lateral joint member, and through said central opening in said central section of said upper end of said lateral wing of said foot bed portion to hingedly connect said lower end of said lateral wing of said ankle cuff to said upper end of said lateral wing of said foot bed member;

said flat flexible medial joint member and said flat lateral joint member yieldably resisting the plantarflexion and dorsiflexion hinged movement between said foot bed member and said ankle cuff with said flat flexible medial and said flat lateral joint members increasingly yieldably resisting the plantarflexion and dorsiflexion hinged movement between said foot bed member and said ankle cuff as the plantarflexion and dorsiflexion hinged movement therebetween increases;

said outer side of said upper end of said medial wing of said foot bed member and said inner side of said lower end of said medial wing of said ankle cuff permitting a limited amount of inversion and eversion movement therebetween;

said outer side of said upper end of said lateral wing of said foot bed member and inner side of said lateral wing of said ankle cuff permitting a limited amount of inversion and eversion movement;

said medial spacer-washer and said lateral spacer-washer permitting an additional amount of eversion and inversion movement between said foot bed member and said ankle cuff; and at least one strap attached to said ankle cuff configured to secure a wearer's lower leg thereto.

3. The hinged ankle brace of claim 2 wherein said outer sides of said upper ends of said medial and lateral wings of said foot bed member are outwardly curved.

4. The hinged ankle brace of claim 2 wherein inner sides of said upper ends of said medial and lateral wings of said foot bed member are outwardly curved.

5. The hinged ankle brace of claim 2 wherein said outer sides of said lower ends of said medial and lateral wings of said ankle cuff are outwardly curved.

6. The hinged ankle brace of claim 2 wherein said inner sides of said lower ends of said medial and lateral wings of said ankle cuff are outwardly curved.

* * * * *